United States Patent [19]

Green

[11] 3,999,047
[45] * Dec. 21, 1976

[54] METHOD AND APPARATUS UTILIZING COLOR ALGEBRA FOR ANALYZING SCENE REGIONS

[76] Inventor: James E. Green, Box 734, Fayetteville, Tenn. 37334

[*] Notice: The portion of the term of this patent subsequent to Nov. 26, 1991, has been disclaimed.

[22] Filed: Nov. 25, 1974

[21] Appl. No.: 526,897

Related U.S. Application Data

[63] Continuation-in-part of Ser. No. 286,043, Sept. 5, 1972, Pat. No. 3,851,156.

[52] U.S. Cl. .................... 235/151.3; 128/2 G; 356/39
[51] Int. Cl.² ........................ G01N 33/16
[58] Field of Search ........... 235/151.3, 151.35, 92; 444/1; 324/71 CP; 178/6.8; 128/2 G, 2 L, DIG. 5; 356/39, 42, 201–206, 36; 340/146.3 AC

[56] References Cited

UNITED STATES PATENTS

| | | | |
|---|---|---|---|
| 3,214,574 | 10/1965 | Landsman et al. | 340/146.3 X |
| 3,315,229 | 4/1967 | Smithline | 340/146.3 X |
| 3,327,117 | 6/1967 | Kamentsky | 356/36 X |
| 3,327,119 | 6/1967 | Kamentsky | 356/51 X |
| 3,408,485 | 10/1968 | Scott et al. | 340/146.3 X |
| 3,413,464 | 11/1968 | Kamentsky | 356/36 X |
| 3,549,994 | 12/1970 | Rothermel et al. | 235/92 PC X |
| 3,657,537 | 10/1971 | Wheeless, Jr. et al. | 356/39 X |
| 3,662,176 | 5/1972 | Kamentsky et al. | 356/39 X |
| 3,684,377 | 8/1972 | Adams et al. | 356/36 |
| 3,699,336 | 10/1972 | Ehrlich et al. | 356/39 X |

*Primary Examiner*—Joseph F. Ruggiero
*Attorney, Agent, or Firm*—Richard J. Birch

[57] ABSTRACT

A method and apparatus for analyzing an illuminated subject. In the preferred embodiment, the subject is a stained blood smear. A first signal is produced which represents a first predetermined wavelength band of the subject modified illumination at a region in the subject. A second signal is produced which represents a second predetermined wavelength band of the subject modified illumination at the region. The two wavelength bands are selected to produce differential contrast between at least two different regions in the subject. The two signals are algebraically combined with thresholding to classify the subject regions in at least one of a predetermined number of categories. Further, signal processing is employed to compile partial and complete features for a predetermined region or cell.

12 Claims, 10 Drawing Figures

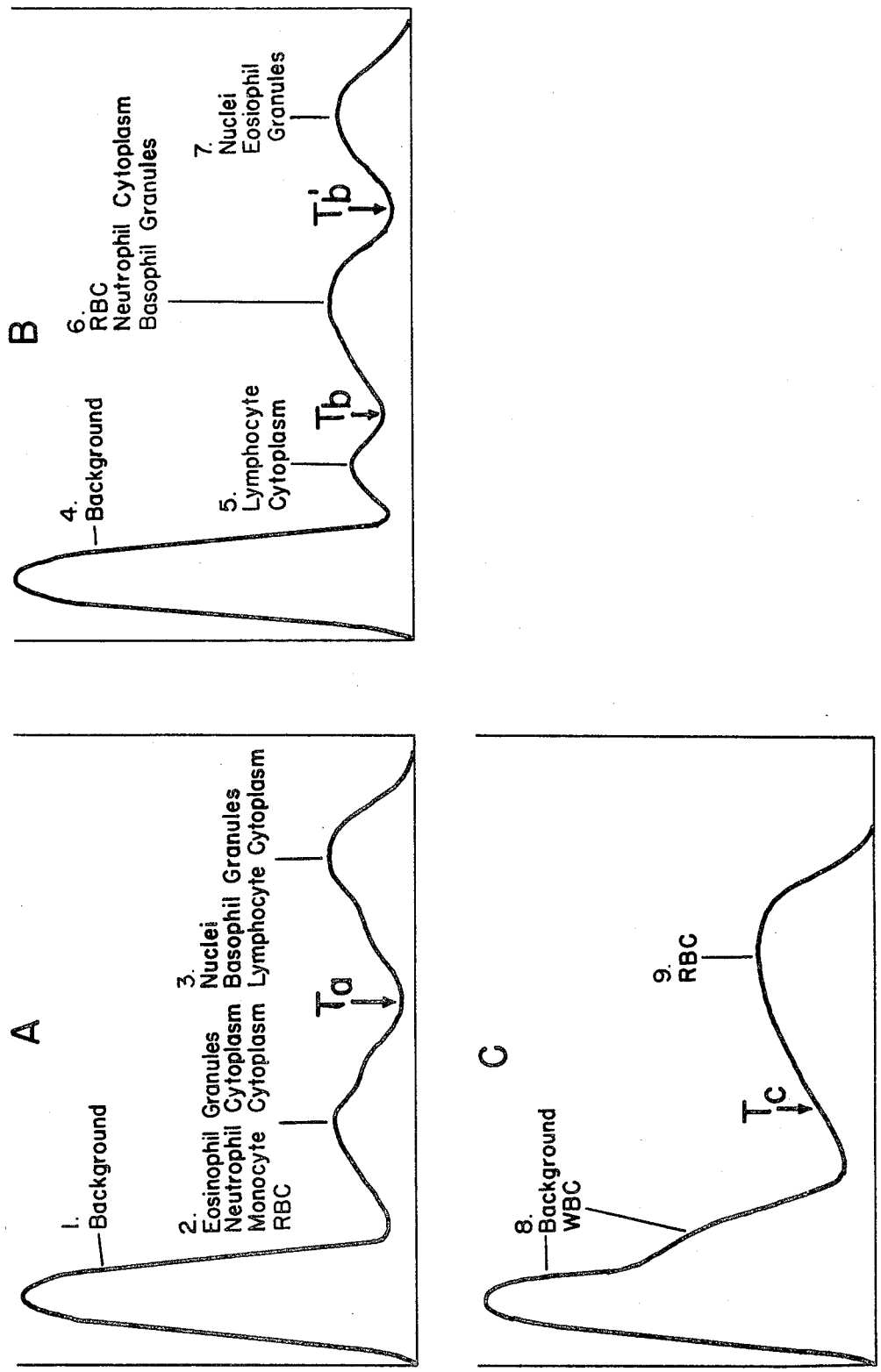

METHOD AND APPARATUS UTILIZING COLOR ALGEBRA FOR ANALYZING SCENE REGIONS

CROSS-REFERENCE TO RELATED APPLICATION

The present application is a continuation-in-part application of my corresponding application Ser. No. 286,043 filed Sept. 5, 1972, for ANALYSIS METHOD AND APPARATUS UTILIZING COLOR ALGEBRA AND IMAGE PROCESSING TECHNIQUES, now U.S. Pat. No. 3,851,156, issued Nov. 26, 1974.

BACKGROUND OF THE INVENTION

The present invention relates to subject analysis methods and systems in general and, more particularly, to a method and apparatus for particle analysis which utilizes color algebra and image processing techniques.

The preferred embodiment for this continuation in part is almost identical to that in the original application, now U.S. Pat. No. 3,851,156. However, to avoid confusion and numerous referencing, much of the descriptive material in the original application will be repeated here.

The need for an accurate, fast and relatively inexpensive system for analyzing particulate matter entrained in a gas or liquid exists in many fields of current technology. For example, recent activities in the area of pollution analysis and control have emphasized the need for a means for particle identification, classification and morphology analysis. A similar need also exists in the field of medical technology for automating labor intensive medical laboratory procedures, such as blood analysis.

The recent spiraling rise of medical care cost have raised the hope that these costs could be reduced by the application of automation technology to the labor intensive procedures used in the medical field. One of the most fundamental tests performed in the most cursory examination or treatment of a patient is blood analysis. Blood has three major particle components: red blood cells (RBC), white blood cells (WBC) and platelets, suspended in a fluid (plasma). An analysis of the relative and absolute quantities of these particles, and additional information regarding their morphology (form and structure) provide considerable insight into the state of health of the patient.

At the present time, several companies have successfully developed and marketed instruments for automated blood analysis. Technion's SMA system for plasma analysis and Hemalog System for cell analysis, and Coulter Electronics' Model S cell counter are well known examples. Using different technologies, the Hemalog and Coulter S generally provide a cost-competitive count of the various particle constituents present in a blood sample. The basic concept, common to both techniques, involves flowing a thin column of diluted blood past a sensor which detects whether a solid particle is present in the liquid medium. This concept, commonly called "flow-through", provides a count of the particles present, but does not provide any qualitative information regarding the identity of these particles or of their morphology.

Therefore, it is necessary to pre-segregate the sample to determine whether the instrument is counting a RBC or a WBC. These two types of cells have significantly different chemical properties, so they can be separated relatively easily. However, it is not possible to further automatically differentiate these cells according to their individual morphological differences using currently available commercial technology.

Nevertheless, such a differentiation is extremely important in about 25 percent of all hospital patients, and it is highly desirable in 50 percent of the patients. This is particularly true of the numerous types of WBC's whose relative concentration and individual morphology are extremely important. Of lesser importance, but still significant is the detection of abnormal red cell morphology. These measurements, commonly known as the "Differential" count, are currently performed by manual labor.

There are two basic approaches to differentiating a single cell by morphology; a direct or pattern recognition approach and, an indirect approach. The latter relies on there being indirect signatures of chemical differences which have a high degree of correlation with the direct signature of morphological differences in the basic WBC's types. Technion's Hemalog-D, employs this approach, using enzymatic stains as the chemical signature to separate five basic WBC types.

As in all indirect techniques, there are both theoretical and practical sources of error. For example, abnormal variations within any of the five basic WBC groups cannot be detected. In a high risk hospital population, 10 to 20 percent of the patients may have relatively normal distribution among the five chemical groups, but still have morphological abnormalities indicative of a pathology. In other words, the morphological/chemical correlation is incomplete, resulting in false negatives, the most serious type of error. Furthermore, a percentage of any healthy population will have unusually low enzyme levels with no accompanying morphological abnormalities or clinical symptoms thus resulting in uneconomical false positives. In addition, the important RBC morphology is not provided by the indirect technique.

In the direct approach, the morphology of the particles or cells is examined directly using computer pattern recognition techniques. Performing the blood cell differential measurement using pattern recognition techniques is within the current state of the Corning, Geometric Data Corp., and Coulter have announced instruments using these techniques. However, these early instruments, in order to be practical from a cost standpoint utilize designs which are too slow and do not automate the analysis of abnormal white blood cells or red blood cells. The same general problems exist in other fields of technology employing particle analysis techniques.

It is, accordingly, a general object of the invention to provide an improved system for subject analysis.

It is a specific object of the invention to provide a particle analysis system which employs color algebra in conjunction with image processing techniques to analyze scene regions.

It is another specific object of the present invention to provide, as one embodiment thereof, a commercially feasible automated blood differential measurement system.

It is a further object of the present invention to employ color algebra techniques which permit the use of simplified algorithms to analyze scene regions.

It is still a further object of the present invention to provide an automated blood differential measurement system which employs scanning and data processing components which, in conjunction with color algebra techniques, drastically reduce both the computer capacity requirement and the processing time.

It is a feature of the present invention that the automated blood differential measurement system embodiment provides increased accuracy over existing systems due to the inherent superiority of a direct measurement technique over an indirect measurement technique together with the additional ability to make finer distinctions between WBC's in any one of the five basic types, the ability to recognize abnormal v. normal morphology; the ability to provide RBC measurements; and the ability to distinguish between cell regions and other scene regions.

It is still another feature of the blood analysis embodiment of the present invention that conventional blood staining procedures can be employed with the color algebra technique of the invention.

These objects and other objects and features of the present invention will best be understood from a detailed description of a preferred embodiment thereof, selected for purposes of illustration, and shown in the accompanying drawings, in which:

FIGS. 2A through 2C are representative histograms of a blood sample; and,

Figure 1A:
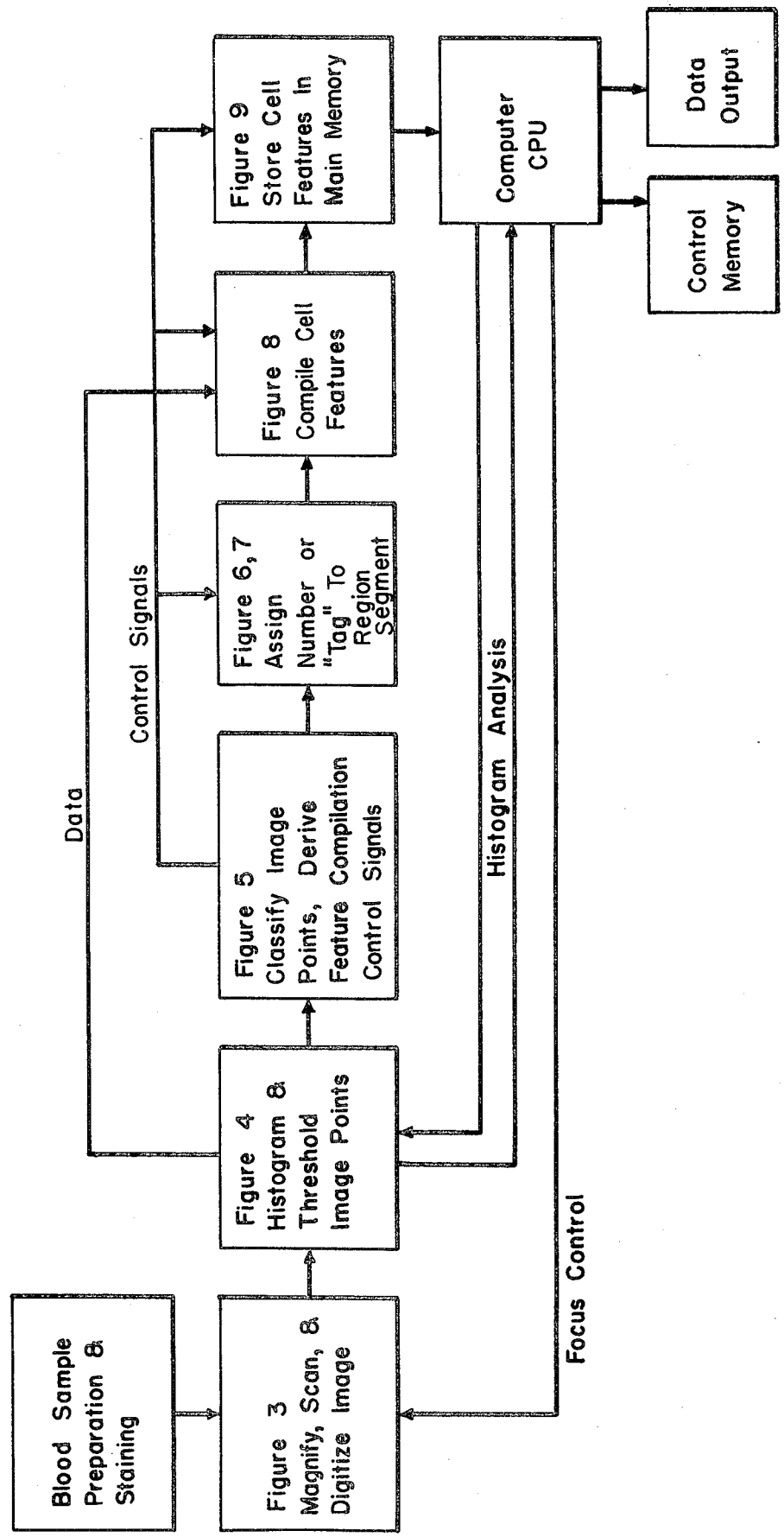
FIG. 1A is a functional block diagram of the blood analysis embodiment of the invention.

The particulate matter analysis system of the present invention can be used for analyzing many different types of particulate matter. However, for purposes of illustration and ease of description, the following discussion will be directed to the blood analysis embodiment of the particulate matter analysis system as shown in functional block diagram form in FIG. 1.

The present invention utilizes color algebra techniques to reduce both the computer capacity requirement and the processing time. Before proceeding with the detailed description of the present invention, it will be helpful to briefly review some basic information with respect to "color".

The perception of color is a complex physiological phenomenon which occurs in response to variations of the spectral components of visible light impinging upon the retina. The quantitative description of color is complicated by the fact that the same perceived color can be produced by numerous combinations of different spectral components.

In order to standardize the description of colors in scientific work, a system of "chromaticity" measurements was developed by the C.I.E. (Commission Internationale de l'Eclairage) in 1931. The chromaticity measurements are obtained by convolving the spectral components of the illumination with three specific spectral distributions to produce "Red", "Green", "Blue" intensities. The percent fraction of each of these intensities is expressed as X, Y, and Z coordinates, respectively, where:

$$X = \frac{R}{R + G + B}$$

$$Y = \frac{G}{R + G + B}$$

-continued
$$Z = \frac{B}{R + G + B}$$

The three spectral distributions have been established so that any combination of wavelengths which produces the same subjective color will also produce the same chromaticity coordinates.

The three components X, Y, and Z, generally corresponding to the fraction of Red, Green and Blue light in the illumination, can be plotted on a two dimensional graph. Chromaticity coordinates have been used in the past as one or more features in multi-dimensional feature space pattern recognition systems to recognize and classify, among other things, blood cells.

Biological specimens are stained to improve contrast of the normally transparent tissues, and render various structures more recognizable. Blood cells are normally stained with a Romanovsky type stain, e.g., Wright's stain, a two component stain system comprising a red and blue dye. The blue stain component stains cell nuclei, the cytoplasm of lymphocytes, and certain granules in the cytoplasm of some of the other cells, in particular the basophilic granules of the basophils. The red stain component is absorbed by the red cells, lightly by the cytoplasm of most white cells, by eosinophil granules and to some extent cell nuclei. These staining patterns are not absolute or mutually exclusive because almost every cell part absorbs both stain components to some extent. However, usually one or the other stain component is predominant and this predominance forms the basis of a functional analysis system utilizing the color differences. Thus, the cytoplasm of most cells, with the exception of lymphocytes, is stained light violet to red-orange, the cytoplasm of lymphocytes is stained a pale blue, the nucleus of the cells is stained a deep purple, the eosinophil granules are stained a deep red to orange, and the basophil granules are stained deeply blue.

For blood cells that have been stained with Wright's stain, the red absorption peak of methylene blue and its derivatives occurs at about 570-600 n.m., the blue absorption peak of the Eosin-Y stain component occurs at about 500-530 n.m. and finally, the "blue-violet" natural absorption peak of hemoglobin occurs at about 400-420 n.m.

The present invention utilizes this color information to generate information with respect to the "differential contrast" between and/or among various points or regions in the cell. The color information is reduced to a differential contrast information by illuminating the sample with white light with subsequent filtration by narrow wavelength band filters. Alternatively, the differential contrast information can be produced by illuminating the blood sample with selected narrow wavelength bands of light.

Each point or region in the cell will modify the light in accordance with its absorption, transmission and reflectivity characteristics. The term "contrast" refers to a substantial difference in the modification of the light by two or more cell points or regions at one wavelength band. The term differential contrast refers to a dissimilar pattern of contrasts at two or more wavelength bands.

The appropriate wavelength bands are selected with respect to the spectral content of the stain or dye system's light modifying characteristics and/or with respect to the light modifying characteristics of the natural material, e.g. hemoglobin. With appropriately selected wavelength bands, the desired differential contrast of the various cell points or regions to be recognized is established by their marked density and/or reflectivity differences. Thus, when the wavelength bands are properly chosen, a particular cell region, such as WBC cytoplasm will be very dense at one wavelength band and relatively transparent at another. Another region such as, RBC cytoplasm will display a different contrast pattern at the same wavelength bands. The differential contrast of the cell components established by the choice of the various wavelength bands permits the identification and classification of cell components or regions by means of a "color algebra" illustrated below.

The color algebra can be implemented by sampling and digitizing the signal representing the sample modified illumination at each of the wavelength bands to produce a digitized serial data stream, and then histogramming the digitized values as shown in FIG. 2. Characteristically, the histograms of the points in the scanned blood sample exhibit two or more groups of points, or peaks at different density levels. For example, as shown in FIG. 2, the peaks may correspond to a group of background points at about the same density, or to another group of somewhat denser cell cytoplasm points or possibly to a third group of very dense cell nucleus points. Several types of cellular components may be combined into a peak at one wavelength, but will be separated at another wavelength. For example, in FIG. 2, WBC and RBC nuclei, basophil granules and lymphocyte cytoplasm are combined in peak 3 of histogram A, but are separated into peaks 5, 6 and 7 of histogram B.

In practice, histogramming has proved to be a feasible method for establishing thresholds. However, it should be understood that the color algebra also can be implemented by arbitrarily establishing the thresholds without sampling, digitizing or histogramming. For example, a suitable color algebra can be used to detect sample regions of blood cells flowing in a liquid stream past a sensor. In this situation, no scanning, sampling, and digitizing or histogramming is employed.

Thresholds are established to separate the peaks of the histograms. The thresholds are shown as $T_A$, $T_B$, and $T_C$ with $T'_B$ illustrating the use of multiple thresholds. Any point in the digitized data stream can then be characterized as a thresholded signal in binary form as exceeding or not exceeding the various thresholds.

The thresholded signals can be combined to produce the following color algebra:

|  | A | B' | B | C |
|---|---|---|---|---|
| Background | 0 | 0 | 0 | 0 |
| RBC Cytoplasm | 0 | 0 | 1 | 1 |
| RBC Neucleus | 1 | 1 | 1 | 1 |
| WBC Neucleus | 1 | 1 | 1 | 0 |
| Monocyte cytoplasm | 0 | 0 | 1 | 0 |
| Neutrophil |  |  |  |  |
| Eosinophil Granules | 0 | 1 | 1 | 0 |
| Basophil Granules | 1 | 0 | 1 | 0 |
| Lymphocyte Cytoplasm | 1 | 0 | 0 | 0 |

This color algebra is applicable for the previously discussed example of a Wright's stained blood sample and the wavelength bands set forth above. Other color algebra can be employed to classify cell components stained with other dye systems or using the characteristic absorption of other natural cellular constituents the wavelength bands again being selected to provide differential contrast between at least two different regions in the sample.

It can be seen from the table that the color algebra characterizes a particular point or region as being in one of a number of cell component classifications. In addition, the color algebra also permits differentiation between cell components and background areas in the blood sample. Thus, the thresholded signals can be algebraically combined to produce sample region classification signals.

The preceding example of a color algebra illustrates the classification of the cell components and background by algebraic combination of the thresholded signals. Alternatively, the signals can be algebraically combined and then thresholded with or without further algebraic combination to produce the Sample Region Classification Signals.

From the preceding description, it will be appreciated that the use of color algebra in the present invention permits the separation of an image into a number of categories of cell components or background without requiring the normal procedure of chromaticity coordinate calculations and subsequent complicated pattern recognition data processing. It also will be appreciated that it is not necessary to stain the cells to use the differential contrast and color algebra features of the present invention. Alternatively, native constituents of the cells may be utilized to provide the necessary contrast patterns. For instance, in addition to the natural absorption of hemoglobin near 400 n.m., the absorption peak of DNA (normally found in cell nuclei) at 258 n.m. and the absorption peak of proteins (normally found predominently in the cell cytoplasm) at 280 n.m. can be used as the wavelength bands. Because of the partial overlap of absorption waves of these two cellular constituents and the presence of some other constituents which also absorb at these wavelengths, the resulting color algebra is somewhat more complicated than that employed with Wright's stain. Furthermore, in using these three wavelength bands, the long experience of the medical community with Wright's blood stain would be lost. For this reason, the Wrights's stain system is the one of choice.

It will further be appreciated that the color algebra feature of the present invention is not limited to three wavelength bands of the preferred embodiment. Any two or more wavelength bands which will produce differential contrast between at least two regions in the subject of interest can be utilized to produce an appropriate color algebra.

Having described the differential contrast and color algebra concepts as they relate to the present invention, I will now proceed with a description of the general systems concept of the preferred embodiment.

Returning now to FIGS. 1A and 1B, there is shown in block form the general systems concept, the principles of operation and the data flow of the blood analysis embodiment.

In FIG. 1A, the blood sample is prepared for analysis by being spread in a thin layer on a glass slide or other suitable surface and stained with a suitable blood stain. Normally, the prepared slide is magnified by an optical system (microscope) and a portion of the magnified image is scanned and digitized at several wavelength bands. Details of this process will be presented in FIG. 3. The magnified image is then embodied in two or more streams of numbers (the digitized serial data signals) which represent the transmission or density of the image over the raster of points.

There are three basic stages in the process of analysis of the scanned and digitized image: (1) the regions are located or localized; (2) quantitative "features" which characterize the cells in some desirable way are extracted from the localized regions; and, (3) using these features the cells are further classified as normal, abnormal, neutrophil, lymphocyte, etc.

The previous state of the art method for performing these tasks was to store the stream of numbers representing the image density at various points in a computer memory. Then, algorithms stored in the computer would localize the cells, extract the features and classify the cells. As an image contains a large number of points, a large memory was required to store it. Also, since all three stages of the analysis were performed by the computer processor, it was of necessity fast and powerful. Both of these factors required the use of a computer so costly that to actually analyze blood smears in this way would be prohibitively expensive.

The preferred embodiment does not use storage of any of the stream of digitized image points in a computer memory. It makes use of a combination of color algebra and simple precessing circuitry to reduce computer memory requirements to that just sufficient to store only the compiled features of the cells in the image. At the same time, the work the computer must perform is reduced to classification of the cells using the compiled features. Both of these characteristics permit the use of a relatively simple and inexpensive computer. Even so, by relieving the computer of the tedious localizing and feature extraction tasks, the present embodiment is able to operate much faster with a small inexpensive computer than a previous state of the art design which used a large expensive computer.

Figure 1B:
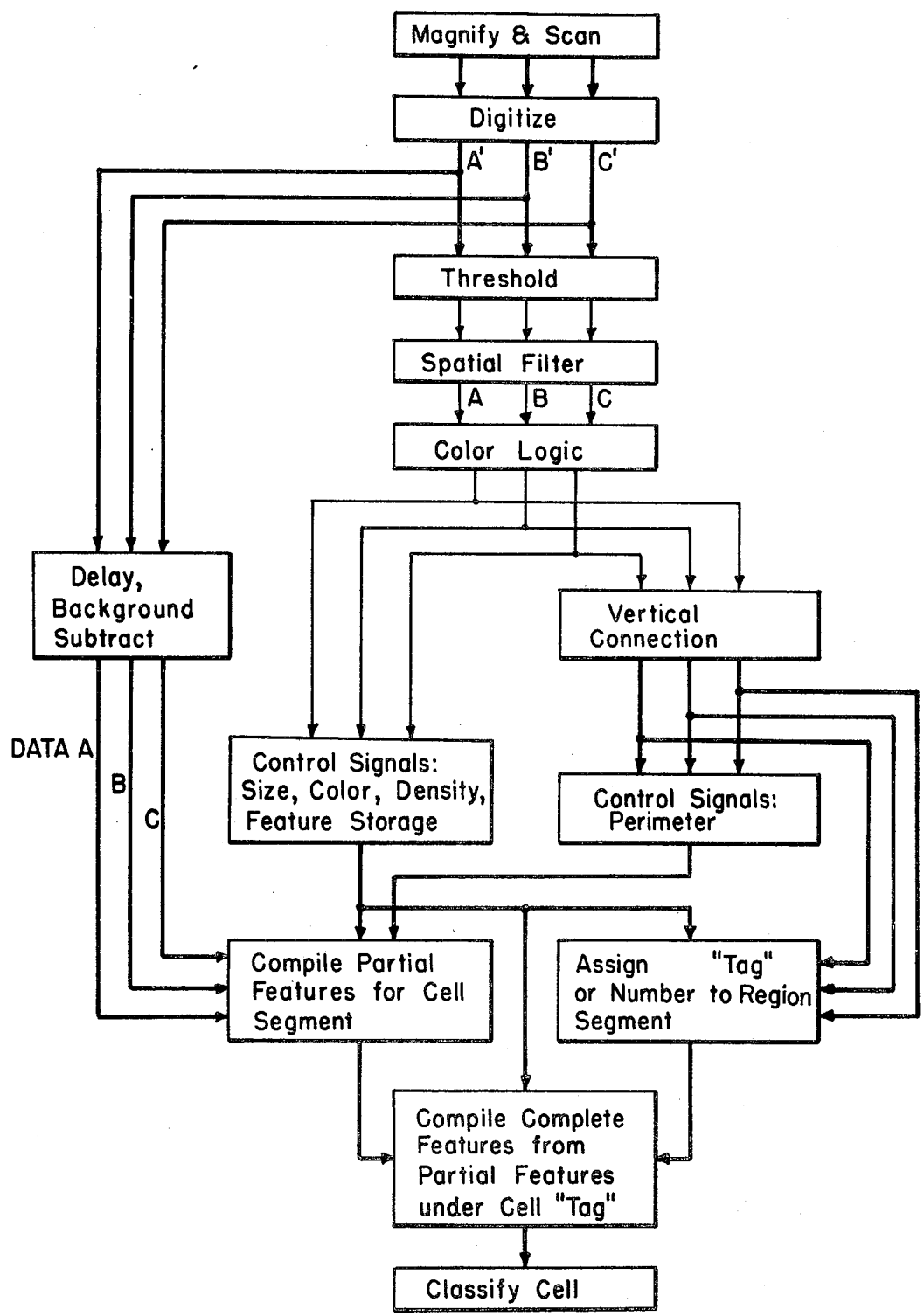
FIG. 1B is a more detailed functional block diagram of the invention showing data flow.

This combination of color algebra and preprocessing of the stream of sampled and digitized points in further illustrated in the block diagram in FIGS. 1A and 1B. The points of each color representation of the digitized image (the Digitized Serial Data Signals) are histogrammed and thresholded to produce Thresholded Signals. The background density is subtracted from the image density to produce a "Data" signal. Using color algebra, each image point is then classified as either background, neucleus, WBC cytoplasm or RBC to produce Sample Region Classification Signals. In the preferred embodiment, a line delay is employed to re-establish the vertical connection of two adjacent image lines. The Sample Region Classification Signals are then used to derive Control Signals for identifying all segments on each scan line and for compiling the cell features for each cell segment on a line-by-line basis. Details of these Control Signals will be discussed and elaborated in FIG. 5.

To keep the features for each encountered cell separate, each scene region in the field is given one of two region numbers or "tags" according to the type of region. Thus, each cell region is given a cell number or tag and each background region is given a background number or tag. Circuitry to assign these tags, and correct errors which might occur, as discussed and elaborated upon in FIGS. 6 and 7.

Figure 8:
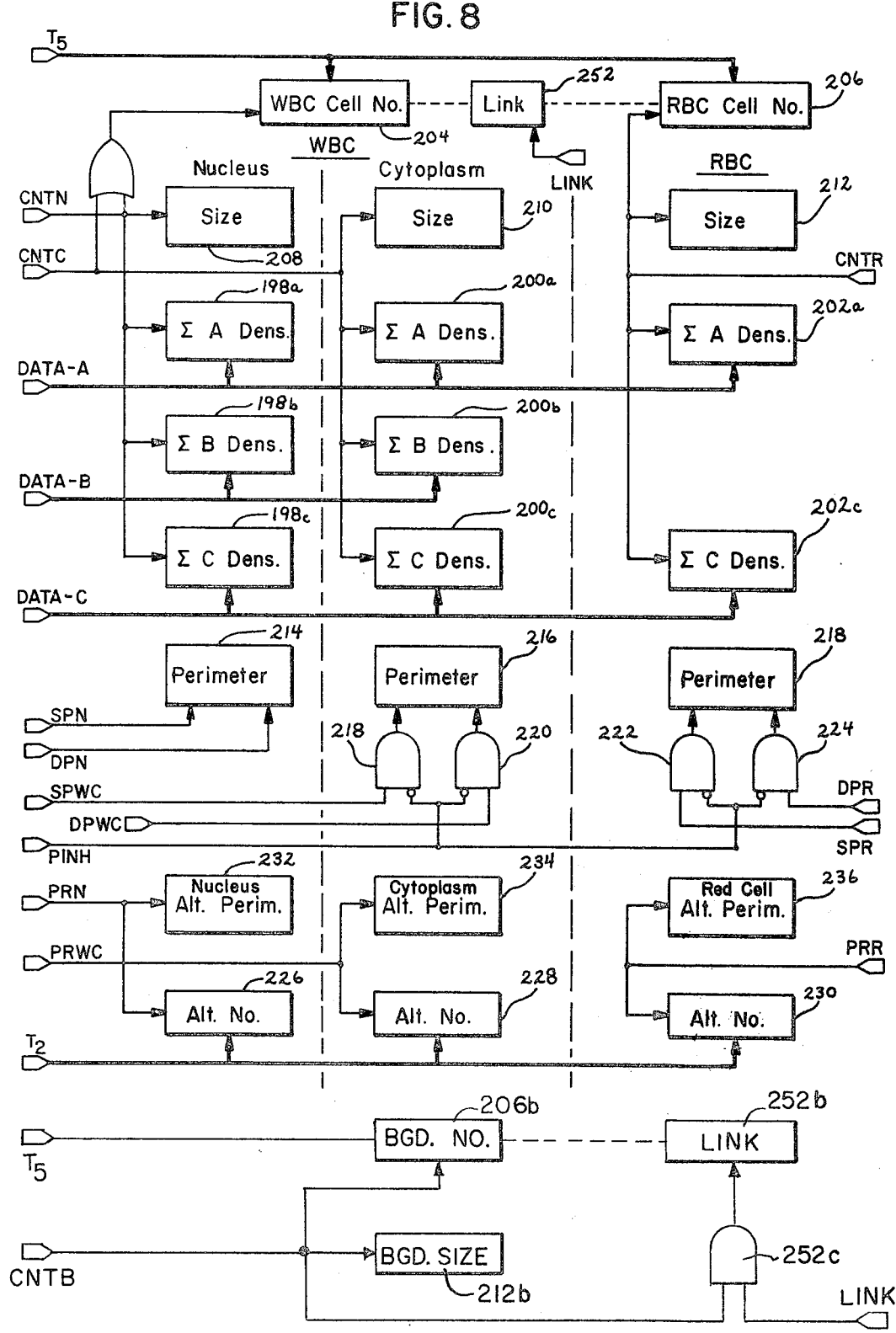
Figure 9:
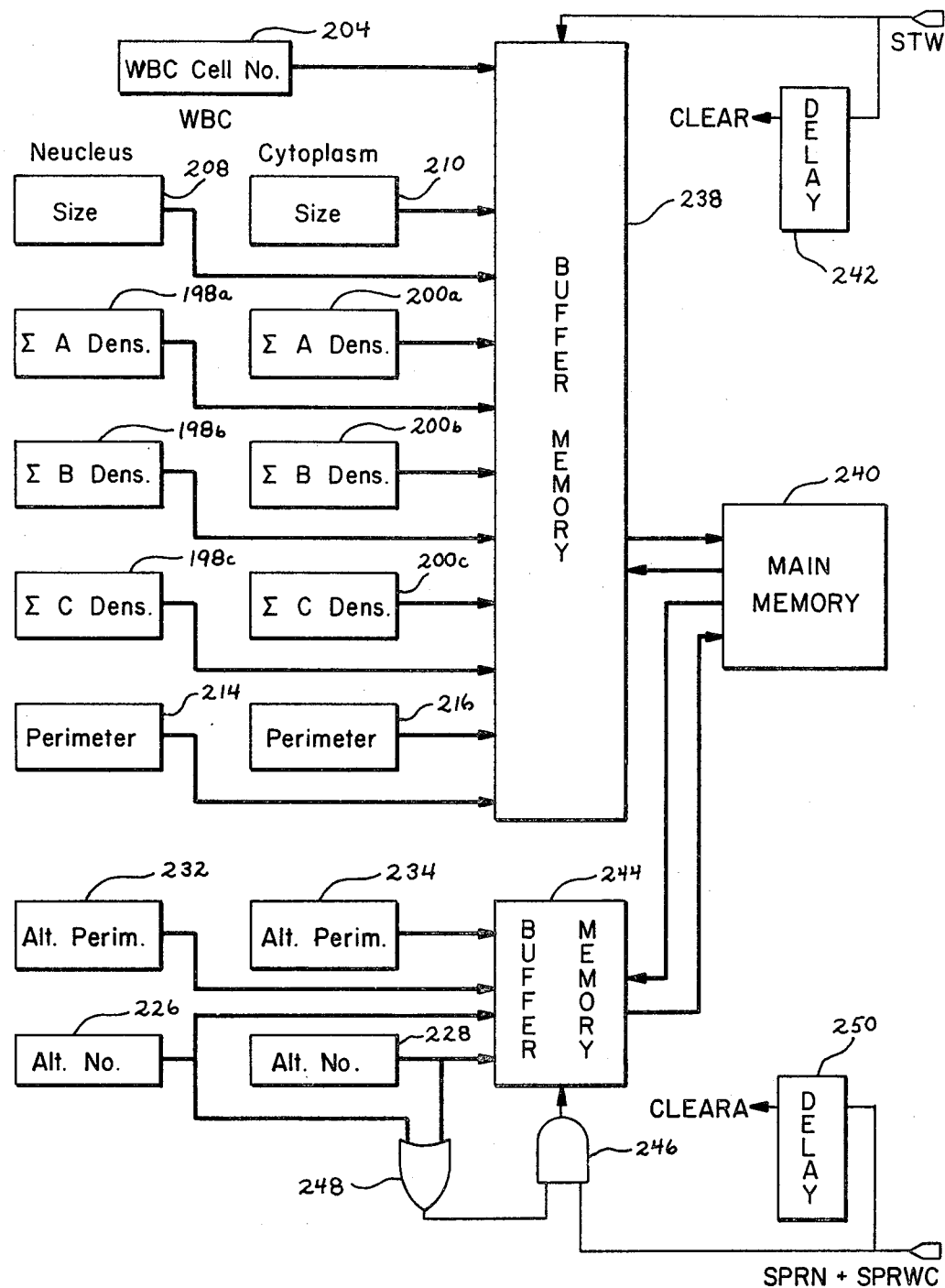

The actual compilation of the partial features for each cell segment on a line-by-line basis is performed by the special circuitry shown in FIGS. 8 and 9. Using the FIG. 5 Control Signals, this circuitry operates on the Data Signals and produces the proper measures of size, shape, density and color of the individual cells and cell inclusions. The complete cell features are stored in a section of the computer memory reserved for each tagged cell number, or nonzero background number.

At the end of the scan of the image, the pre-processor has completed the compilation of the complete cell features for each cell encountered in the image and these features are stored under appropriate numbers or tags in the main memory. The computer then has only to further classify the cells, usually by multidimensional feature space analysis familiar to the art, to produce the differential count data output. The instructions which perform this further classification and perform overall system moritoring are shown residing in a separate "control memory". System monitoring functions include moritoring the histograms and the compiled features to insure that the sample has been properly stained and that the system is performing within predetermined operating parameters, keeping track of the patient's identification, monitoring the focus control, summarizing data over a large number of cells, and averaging and outputting the summarized data.

It will be appreciated from the foregoing and following description that the preferred embodiment is one specific example of a more general method and apparatus for subject analysis characterized by the compilation of partial cell features from a scanned signal representing the sample. The preferred embodiment comprises a sophisticated analysis system which isolates and analyzes each cell in the scene containing many blood cells. In order to accomplish this sophisticated analysis of a complex scene, a number of types of control signals are generated from both normal and delayed signals, the partial cell features are compiled from identified cell and background segments in each scan line and then the complete cell features are compiled from the partial features utilizing cell and background tags which have been assigned to each region in the scene. However, a less complex version of the invention can be employed to analyze a scene containing only one complete cell (or one cell of a particular type, such as a WBC). In this case, a single type of control signal is derived from undelayed signals and are used to compile the partial and complete cell features from the single cell without using cell tags.

Having described the overall systems concept and general operating principles of the preferred embodiment, I will now discuss in detail the specific circuitry of the embodiment.

Figure 3:
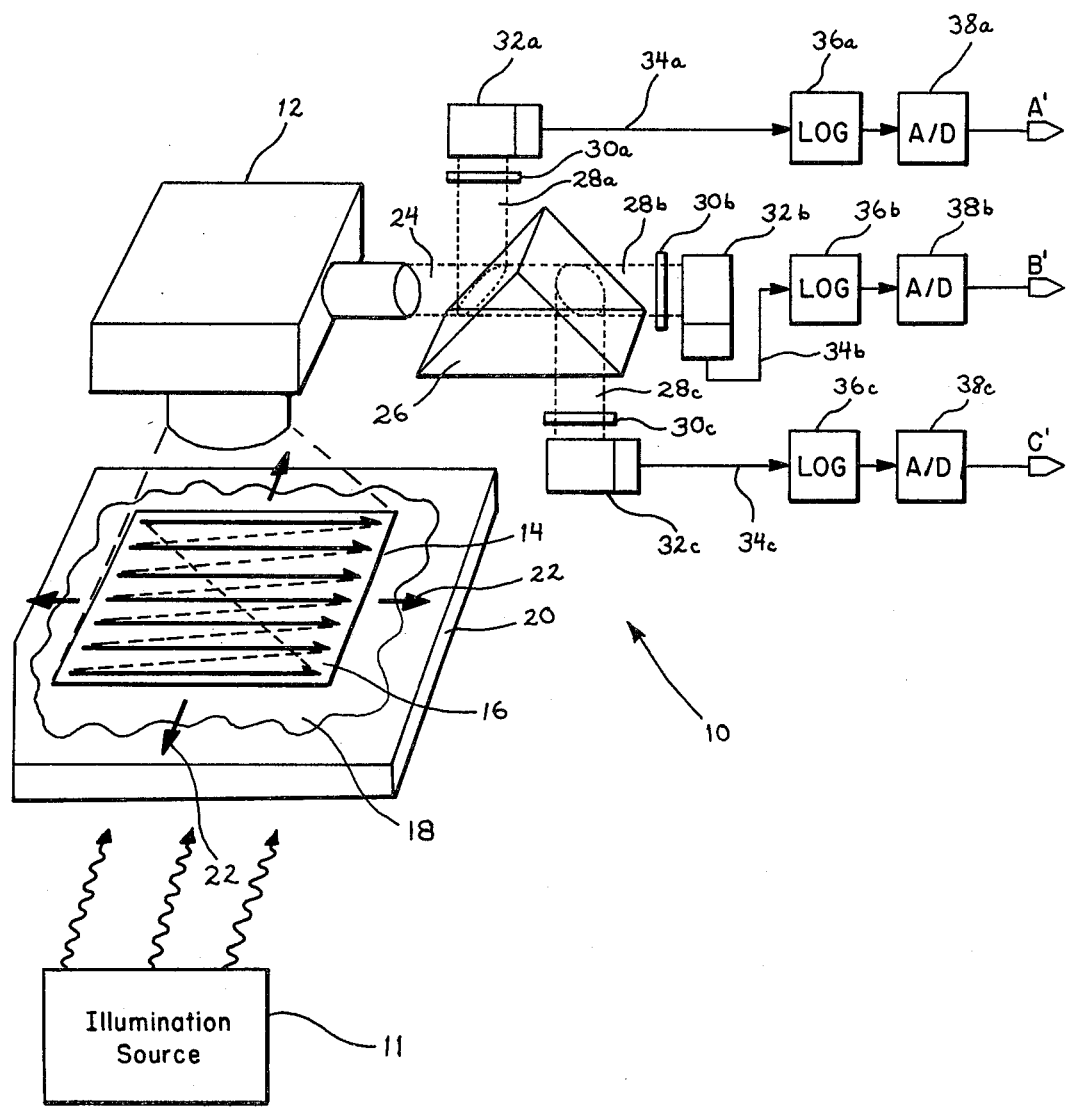
FIGS. 3 through 9 depict in partial block and diagrammatic form the blood analysis embodiment of the invention.

Referring to FIG. 3, there is shown in diagrammatic and partial block form an optical-to-electrical input stage for the blood cell analysis system which is indicated generally by the reference numeral 10. An optical scanner 12 scans in raster fashion a field 14 which contains a blood cell sample 16. The sample 16 comprises a blood film composed of red cells, white cells, and platelets spread on a monolayer 18 on a standard glass slide 20.

The blood layer 18 is stained with a suitable stain which enhances the morphological components of the blood cells. A typical example of such a stain is the previously mentioned Wright's stain. The stained blood layer 18 is scanned within field 14 by means of the optical scanner 12. For purposes of illustration, the spacing between the scan lines shown in FIG. 3 has been greatly exaggerated and the relative movement of the field 14 across the blood sample 16 has been indicated by relative movement arrows 22. Furthermore, the optical system within scanner 12 has been generalized in the drawings. It will be appreciated that suitable magnification stages and focusing control systems, e.g., a microscope input to scanner 12 can be and normally would be, employed in the blood analysis embodiment of the invention.

The blood sample 16 is illuminated by light from an illumination source 11. The sample can be illuminated directly to provide reflective modification of the light by the blood sample or from beneath to provide transmissive modification of the light. It will be appreciated that a fluorescent stain can be employed to provide the desired modification of the illumination.

The scanned output beam 24 from scanner 12 is passed through a beam splitting prism 26 which divides the output beam 24 into three separate beams 28a, 28b, and 28c. Each beam 28 passes through the previously mentioned color filters 30a, 30b, and 30c and impinges upon photo tubes 32a, 32b, and 32c. Alternatively, dichroic coatings can be used on the beam splitting prism 26 to achieve the desired color separation. The electrical signal from the photo tube 32 on output lines 34a, 34b, and 34c represents in electrical form the optical transmission of each segment of the scanned field 14. The optical transmission (linear) is converted to optical density (logarithmic) be means of log-converters 36a, 36b, and 36c. The analog output of the log-converters 36 is converted into a Digitized Serial Data Signal at a specified sampling interval by means of A/D converters 38a, 38b, and 38c. The outputs from A/D converters 38a, 38b, and 38c are identified in FIG. 1 as Digitized Serial Data Signals labeled A', B', and C'.

Figure 4:
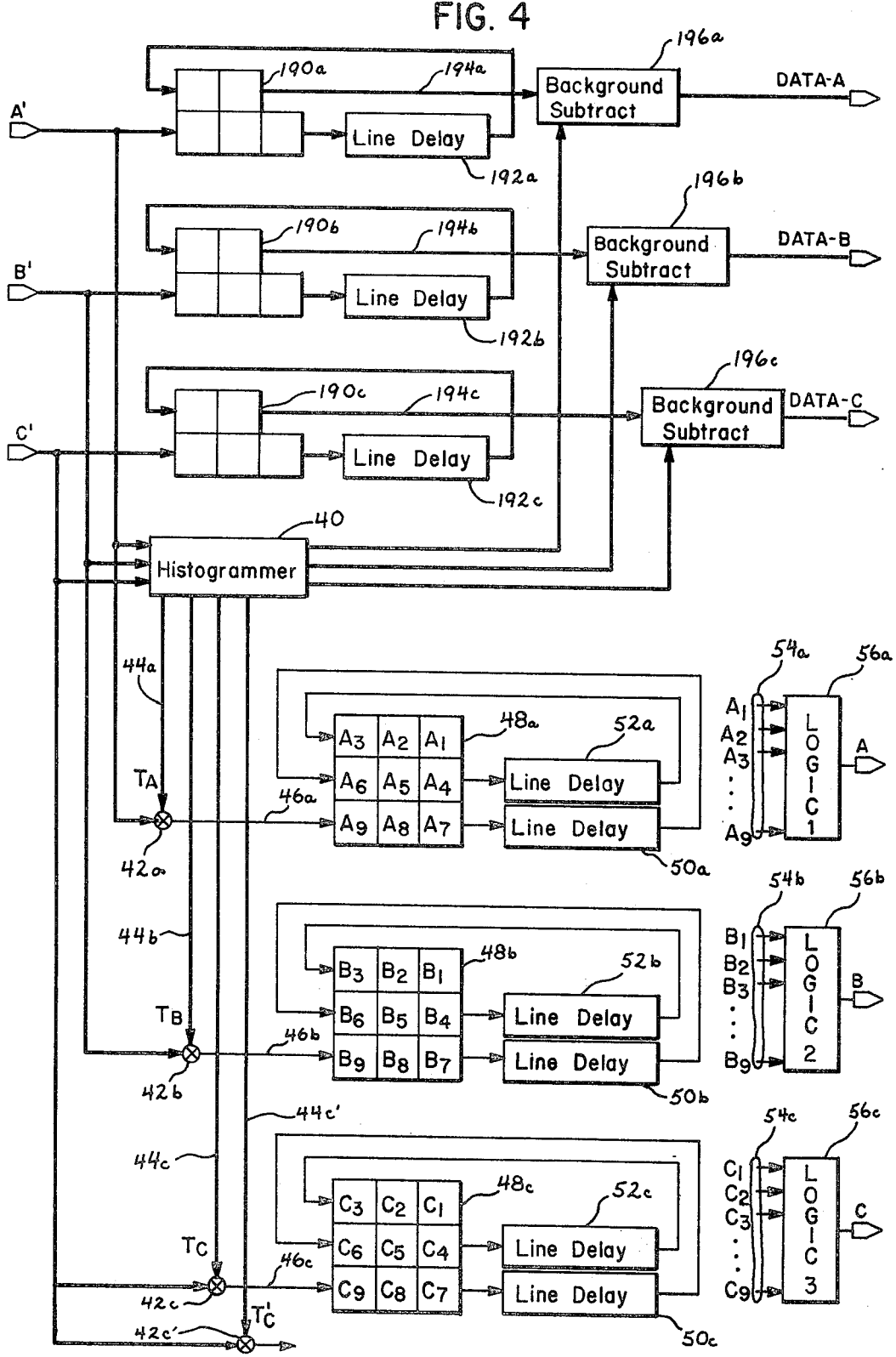

Looking now to FIG. 4, the three channel data A', B' and C' is applied as an input to a histogrammer 40 and to corresponding signal level comparators 42a, 42b, and 42c. During the first pass of scanner 12 through field 14, the histogrammer 40 collects the histographic information within the field for each signal, i.e., the density distribution of the points within the field 14. The three histograms are thresholded and during the second scan of the field the thresholded outputs $T_A$, $T_B$, and $T_C$ are applied to output lines 44a, 44b, and 44c as the second input to the corresponding comparators 42a, 42b and 42c. The magnitude of the optical density data A', B', and C; is thus compared with the preset thresholds $T_A$, $T_B$, and $T_C$ to produce thresholded signals. The potential for thresholding a data signal more than once is illustrated in FIG. 2 by the label $T'_C$ and comparator 42c'.

The output from each of the comparators 42a, 42b, and 42c is a ONE if the corresponding input is equal to or greater than the preset threshold $T_A$, $T_B$, or $T_C$ (an "over-threshold" signal) and ZERO if less than the threshold (an "under-threshold" to signal). The thresholded signal output from each of the three channel comparators on output lines 46a, 46b, and 46c is a one-bit datum representing the presence or absence of an over-threshold signal.

For purposes of clarity in the drawings, relative shading has been used on input and output lines to designate the type of signals thereon. Thus, looking at FIG. 4, a multiple number of bits is indicated by a heavy line, such as, the output lines 44 from the histogrammer 40 while a one bit date line is indicated by a relatively light line such as lines 46a, 46b, and 46c.

The thresholded signals on comparator output line 46a is applied to a 3 × 3 shift register array 48a. Selected outputs from the 3 × 3 array are inputted to line delays 50a and 52a. The line delays can be implemented in a variety of ways including delay lines, shift registers, etc. The outputs from the line delays 50a and 52a are fed back to the 3 × 3 shift register array 48. The separate sections within the 3 × 3 array are identified by the letter "A" with suitable subscripts 1 through 9. The timing of the 3 × 3 array and the line delays 50a and 52a is designed to provide a total delay of two scan lines through field 14 plus the time delay represented by shifting the one bit data signal through three of the blocks in the 3 × 3 array 48a. Thus, a one line delay for field 14 corresponds to the delay produced by $A_9$, $A_8$, $A_7$ and line delay 50a.

Given this delay configuration for the 3 × 3 array 48a and the corresponding line delays 50a and 52a, it will be appreciated that the 3 × 3 array 48a restores the vertical connection of points in three adjacent lines within the scanned field by delaying two lines. The signals within the 3 × 3 array blocks $A_1$ through $A_9$ are applied to corresponding input lines identified collectively by the reference numeral 54a to a logic circuit shown in block form in FIG. 4 and identified by the reference numeral 56a. The logic circuit 56a performs a spatial filtering function with respect to the center element $A_5$ in the 3 × 3 array. Normally, the output signal A from logic circuit 56a is the same as the center element $A_5$ in the 3 × 3 array 48a. However, if the center element $A_5$ is ZERO and all or most of the surrounding elements $A_1$ through $A_4$ and $A_6$ through $A_9$ are ONE, the logic circuit 56a will change the value of the output signal A to a ONE. Conversely, if all or most of the elements surrounding a ONE center element are ZEROS, then the value of the center element $A_5$ is changed to ZERO for the output signal A from logic circuit 56a. The same filtering is performed for the signals on input lines 46b and 46c. For purposes of clarity, the same reference numerals have been used in FIG. 4 with the corresponding small letter designations for the b and c channels. An example of such filtering follows:

| Value of Element 5 | NUMBER OF SURROUNDING O's | | | | | | | | |
|---|---|---|---|---|---|---|---|---|---|
| | 0 | 1 | 2 | 3 | 4 | 5 | 6 | 7 | 8 |
| 0 | 1 | 1 | 1 | 0 | 0 | 0 | 0 | 0 | 0 |
| 1 | 1 | 1 | 1 | 1 | 1 | 1 | 0 | 0 | 0 |

The A, B, and C outputs from the corresponding circuits 56a, 56b, and 56c are filtered versions of the data in array blocks $A_5$, $B_5$ and $C_5$, respectively.

The spatial filtering provided by the 3 × 3 array 48a, its corresponding line delays 50a and 52a and the logic circuit 56a is optional in the present invention. If a very clean signal with no noise is available, filtering is not necessary. However, since most practical electronic systems are noisy, the preferred embodiment of the present invention includes the filtering circuit just described. The spatial filtering function can be performed at several points in the data analysis. For example, it can be performed after the color algebra as well as before.

Figure 5:
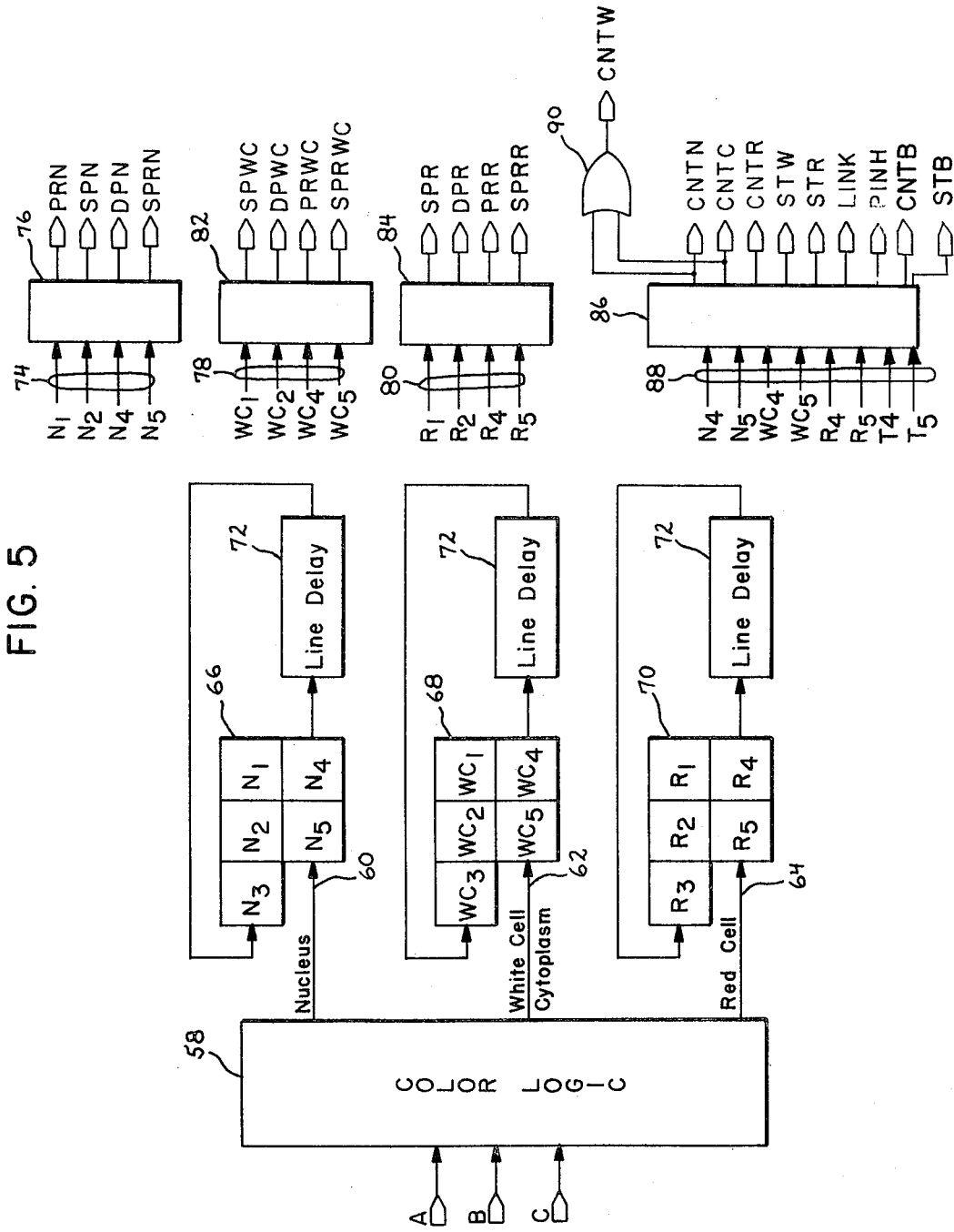

Referring now to FIG. 5, the thresholded and spatially filtered signals A, B, and C from the three logic circuits shown in FIG. 4 are applied as inputs to a color logic circuit 58 shown in block form in FIG. 5. The color logic circuit 58 processes the A, B, and C signals to produce sample region classification signals. In the preferred embodiment, these signals represent points in the nuclei, white cell cytoplasm, red cells and background in the scanned image.

The color algebra performed by color logic circuit 58 is not as complicated as the generalized color algebra described previously. The logic circuit 58 performs the following color algebra:

| Cell Component Type | A | B | C |
|---|---|---|---|
| Background | 0 | 0 | 0 |
| Nucleus (N) | 1 | 1 | $\phi$ |
| WBC Cytoplasm | 1 | 0 | 0 |
|  | 0 | 1 | 0 |
| RBC (R) Cytoplasm | $\phi$ | $\phi$ | 1 |

$\phi$ = don't care

The color logic circuit 58 produces three output or "sample region classification" signals which indicate when a point is part of a cell's nucleus, white cell's cytoplasm or a red cell. These three outputs appear, respectively, on output lines 60, 62, and 64, and are inputted to corresponding five block arrays 66, 68, and 70. Each array is provided with a line delay 72. The purpose of the line delay is to delay the signal and thereby re-establish the vertical connection of the points within the array. Note that a delay of a single line was produced by the signal transition in the 3 × 3 array 48a shown in FIG. 4 as the signal progressed from block $A_9$ to $A_5$. The line delay 72 shown in FIG. 5 then produces another single line of delay. It also should be noted that the point $A_5$ in the 3 × 3 array shown in FIG. 4 and the point $N_5$ shown in the five block array in FIG. 5 correspond to the same point in the scanned field 14.

The outputs from the four array blocks $N_1$, $N_2$, $N_4$ and $N_5$ are applied as inputs, on leads identified collectively by the reference numeral 74, to a nucleus perimeter control logic circuit 76.

The control logic circuit 76 is designed to produce control signals for the system with respect to the perimeters of each detected nucleus. The control circuit 76 generates four control signals: straight perimeter, nucleus (SPN); diagonal perimeter, nucleus (DPN), previous row perimeter, nucleus (PRN); and, store previous row, nucleus (SPRN). The truth table for generating these four control signals is:

4 INPUT ELEMENTS OF LOGIC 76, 82, & 84
USING ARRAY 66 AS AN EXAMPLE

CONTENTS OF 4 ELEMENTS OF 5 BLOCK ARRAY

| 0 | 1 | 2 | 3 | 4 |
|---|---|---|---|---|
| 0 0 / 0 0 | 0 0 / 0 1 | 0 0 / 1 0 | 0 0 / 1 1 | 0 1 / 0 0 |

4 INPUT ELEMENTS OF LOGIC 76, 82, & 84
USING ARRAY 66 AS AN EXAMPLE

CONTENTS OF 4 ELEMENTS OF 5 BLOCK ARRAY

| 5 | 6 | 7 | 8 | 9 |
|---|---|---|---|---|
| 0 1 / 0 1 | 0 1 / 1 0 | 0 1 / 1 1 | 1 0 / 0 0 | 1 0 / 0 1 |

| 10 | 11 | 12 | 13 | 14 |
|---|---|---|---|---|
| 1 0 / 1 0 | 1 0 / 1 1 | 1 1 / 0 0 | 1 1 / 0 1 | 1 1 / 1 0 |

| 15 |
|---|
| 1 1 / 1 1 |

Output of logic 76, 82, & 84:
0: 0, 1, 2, 4, 15, (6, excepting logic 76)
STRAIGHT PERIMETER: 3, 5, 10
DIAGONAL PERIMETER: 7, 11, 13, 14, (6, 9, logic 76 only)
ALTERNATE PERIMETER: 12
STORE ALTERNATE PERIMETER: 8, (9, excepting logic 76)

Similar logic is also applied with respect to the outputs from the white cell cytoplasm five block array 68 and the red cell five block array 70. The respective outputs from these arrays are applied through input lines 78 and 80, respectively, to corresponding control logic circuits 82 and 84. The white cell cytoplasm control logic circuit 82 generates four output signals: straight perimeter, white cytoplasm (SPWC); diagonal perimeter, white cytoplasm (DPWC); previous row, white cytoplasm (PRWC); and, store previous row, white cytoplasm (SPRWC). Similarly, the red cell control logic 84 also produces four outputs namely, straight perimeter, red cell (SPR); diagonal perimeter, red cell (DPR); previous row, red cell (PRR); and, store previous row, red cell (SPRR).

An additional control logic circuit 86 develops control signals based upon input signals from the nucleus, white cytoplasm, red cell and cell tag five block arrays 66, 68, 70, and 92, respectively. The input signals to logic array 86 on input leads 88 comprise the signals from the $N_4$ and $N_5$ blocks of the nucleus array 66: signals from the $WC_4$ and $WC_5$ blocks of the white cell cytoplasm array 68 and, signals from the $R_4$ and $R_5$ blocks of the red cell array 70 and signals from the $T_4$ and $T_5$ blocks of 92 in FIG. 6. The control logic circuit 86 generates nine output signals in accordance with the truth table as follows:

| INTERMEDIATE CLASSIFICATIONS | INPUT | | | |
|---|---|---|---|---|
|  | N | WC | R | T |
| Background, zero (0) | 0 | 0 | 0 | Zero |
| Background, non-zero (NZB) | 0 | 0 | 0 | Non-zero |
| WBC Nucleus (WN) | 1 | 0 | 0 | NA |
| WBC Cytoplasm (WC) | 0 | 1 | 0 | NA |
| RBC Nucleus (RN) | 1 | 0 | 1 | NA |
| RBC Cytoplasm (RC) | 0 | 0 | 1 | NA |

NA = not applicable

TRANSITION OF INTERMEDIATE CLASSIFICATIONS IN ELEMENTS NO. 4 AND NO. 5 IN ARRAYS NOS. 66, 68, 70, and 92

| Transition | | Count | | | | | | Store | |
|---|---|---|---|---|---|---|---|---|---|
| 4 | 5 | N | WC | R | B | W | R | B | LINK | PINH |
| 0 | 0 | 0 | 0 | 0 | 0 | 0 | 0 | 0 | 0 |
| WN | WN | 1 | | | | | | | |
| WC | WC | | 1 | | | | | | |
| RN | RN | 1 | | | | | | | |
| RC | RC | | | 1 | | | | | |
| O | WN | 1 | | | | | | | |
| O | WC | | 1 | | | | | | |
| O | RN | 1 | | | | | | 1 | |
| O | RC | | | 1 | | | | | |
| WN | O | | | | | 1 | | | |
| WC | O | | | | | 1 | | | |
| RN | O | | | | | 1 | | | |
| RC | O | | | | | | 1 | | |
| WC | RC | | | 1 | | 1 | | | |
| RC | WC | | | | | 1 | | | |
| WN | WC | | 1 | | | | | | 1 |
| WC | WN | 1 | | | | | | | 1 |
| RC | RN | 1 | | | | | | 1 | 1 |
| RN | RC | | | 1 | | | | | 1 |
| RC | WN | 1 | | | | | | 1 | |
| WN | RC | | | 1 | | | | | 1 |
| RN | WN | 1 | | | | | | | |
| WN | RN | 1 | | | | | | | |
| RN | WC | | 1 | | | | | | |
| WC | RN | 1 | | | | | | 1 | |
| RC RN | NZB | | | 1 | 1 | | | 1 | 1 |
| WC WN | NZB | | | 1 | 1 | | | 1 | 1 |
| NZB | RC | | | 1 | | | 1 | | 1 |
| NZB | WN | | | | | | | | |
| | RC | 1 | | | | | 1 | | 1 |
| NZB | WC | | 1 | | | | 1 | | 1 |

The "count" (or "compile partial features") output control signals from logic circuit 86 for the nucleus, cytoplasm, red cells and non-zero background (NZB) are identified in FIG. 5 by the respective abbreviations, "CNTN", "CNTC", "CNTR" and "CNTB".

Three "store" control signals are generated to control the storage of partial white cell feature data (STW), the storage of the partial red cell feature data (STR) and the storage of non-zero background data (STB). The final two output signals from the control logic circuit 86 are a "link" signal (LINK), and a perimeter inhibit signal (PINH). The purpose of these two signals will be explained subsequently. The count nucleus signal (CNTN) and the count cytoplasm signal (CNTC) are applied to an OR gate 90 which produces an output signal for indicating that white cell partial features are being compiled (CNTW).

It can be seen from FIG. 5, that the Perimeter Control Signals from logic circuits 76, 82 and 84 are derived, inter alia, from signals which are delayed by means of line delays 72. However, in a simpler embodiment of the invention, the line delays 72 can be omitted if the sample analysis does not require perimeter information and the concomitant use of perimeter control signals. In such a simpler embodiment, there is also a reduction in the complexity of the cell tagging logic which will be discussed below in connection with FIGS. 6 and 7.

The control signals generated by the logic circuits shown in FIG. 5 are employed to identify an encountered cell segment and to control the compilation of the partial and complete features of the various components of the cells. The partial cell features, such as size, density, shape, perimeter length, inclusions, etc., are compiled on a line-by-line basis for each identified cell segment or non-zero background segment. Each scene region is assigned an appropriate number or tag in order to properly control the compilation of the complete features from the partial features for a particular cell. The region identification number or tag is passed from one row to the next when there are vertically connected points in a region.

As will be elaborated shortly, the main scene background region which is simply connected in the topological sense to the scene border is normally assigned a zero background tag or number. A "Non-Zero Background" is a background region which is not or appears not to be "simply connected" in a topological sense to the main scene background, and which is thus assigned a "non-zero" tag or number.

In practice, a true non-zero background region represents an inclusion in a cell (such as the central pallor in a red cell or a vacuole in a white cell) which is physically as pale as the main background and thus is identified as background by the color algebra. Occasionally a portion of the main scene background region will be incorrectly assigned a non-zero background number because no simple connection to the main background has been encountered at the time the assignment is made. For example, this condition will occur when an inverted U-shaped cell is encounted during a raster scan. However, this error is corrected by the "Equate" and CHG signals when the simple connection is subsequently detected.

Figure 6:
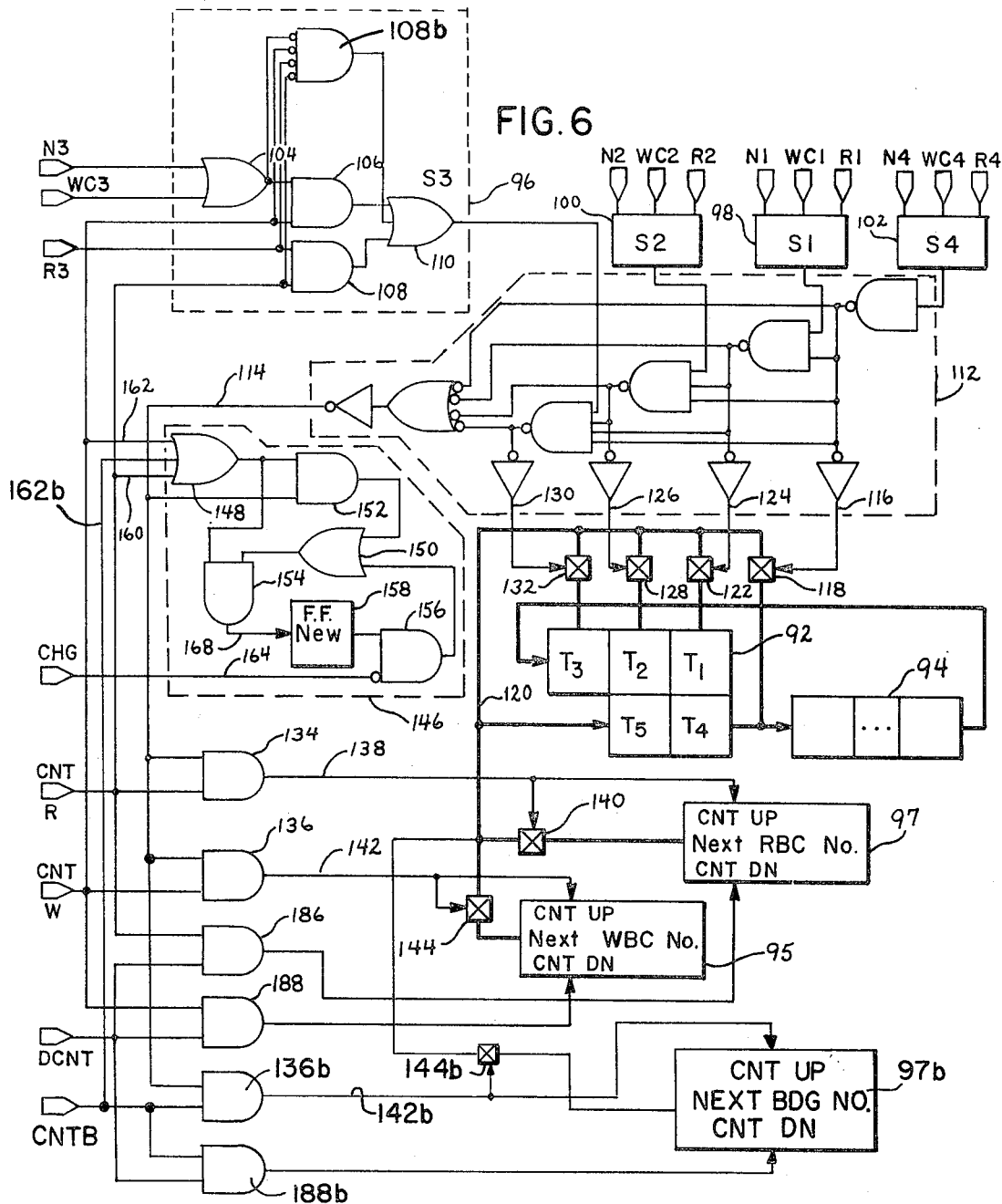
Figure 7:
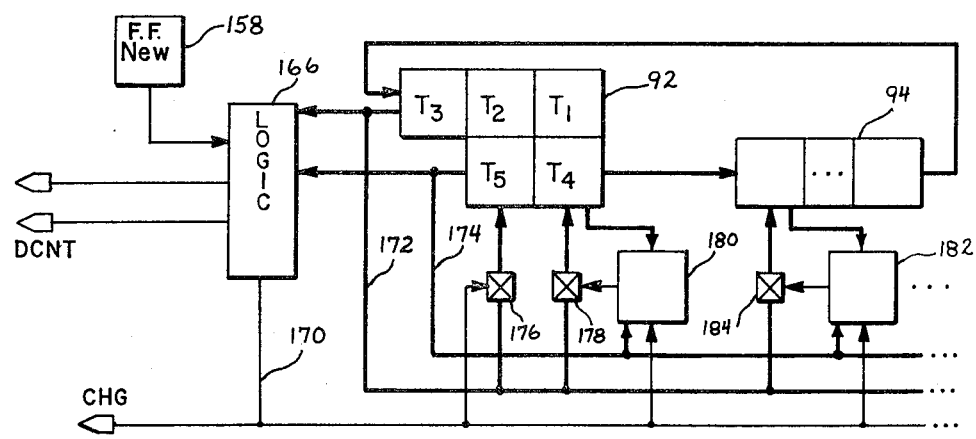

The circuitry shown in FIGS. 6 and 7 is employed to generate and assign the appropriate number or tag to the region. From a functional standpoint, the circuitry must assign a new cell or background number to the cell or background if the cell or background region has not been encountered previously in the scan of the field 14. Conversely, the circuitry must assign the appropriate old cell or background number if the cell or background has been encountered previously. In some situations, the initial data may indicate that a cell or background segment from a new region has been encountered when in fact the segment actually is part of a previously encountered and identified region. When this situation is recognized, the new number must be removed from the segment and the segment tagged with the appropriate old number.

The circuitry which accomplishes the region identification or tagging function is shown in partial block and schematic form in FIG. 6 and in block form in FIG. 7. Referring now to FIG. 6, there is shown a five block tag array 92 and a line delay 94. The five blocks of the tag array are identified as $T_1$ through $T_5$. These blocks correspond to the same portion of the scanned image as $A_1-A_5$, $B_1-B_5$ and $C_1-C_5$ in FIG. 4. From a functional standpoint, the purpose of the tag array 92 and its associated circuitry is to determine if there is any point in the scanned picture of the same type as point $T_5$ which has previously been assigned a number and which is touching point $T_5$. If this is the case, then the point in $T_5$ should be assigned the same number.

The red and white blood cell and background numbers or tags are obtained from corresponding UP-DOWN White and Red Blood Cell and Background counters 95, 97, and 97b, respectively. The operation of these counters will be described below.

Looking at FIGS. 5 and 6, the outputs from $N_3$, $WC_3$ and R of the arrays 66, 68, and 70, respectively, are applied as inputs to a logic circuit 96 which is also identified in FIG. 6 by the designation "S3". The logic circuitry shown in S3 is duplicated in logic circuits 98, 100, and 102, which are designated respectively as "S1", "S2", and "S4". These four logic circuits S1–S4 determine whether each of the points represented by $T_1$ through $T_4$ are of the same region type as the point represented by $T_5$. The inputs to the logic circuits S1–S4 correspond to the same numbered blocks in the nucleus, white cell cytoplasm and red cell arrays 66, 68, and 70, respectively, shown in FIG. 5. Thus, for the S3 logic circuit the inputs comprise the signals from the $N_3$, $WC_3$ and $R_3$ blocks of the corresponding arrays and the count white (CNTW) signals. For purposes of clarity, the count red and count white signals input lines have been omitted from S1, S2 and S4.

In each of the logic circuits S1–S4, and as shown in detail in S3, the nucleus and white cell cytoplasm signals are ORed by OR gate 104 to produce a white cell output. The output of OR gate 104 is ANDed with the signal count white (CNTW, FIG. 5) in AND gate 106 to indicate that $T_5$ and $T_3$ are both white cell points. The $R_3$ and count red cell signal (CNTR, FIG. 5) are also ANDed by an AND gate 108 to indicate that $T_5$ and $T_3$ are both red cell points. The output of gate 104 is also ANDed through inverting inputs in gate 108b with the CNTR, CNTC and $R_3$ signals to indicate that both points are background points. If either "both" red cell points, both white cell points, or both background points are indicated, OR gate 110 will produce a high output.

The same basic logic is performed by logic circuit S1, S2, and S4. A high output from any one of the logic circuits S1 through S4 indicates that the corresponding point in the tag array 92 i.e., points $T_1$ through $T_4$ are of the same cell type as $T_5$. Assuming that one or more of the points $T_1$ through $T_4$ are of the same type as $T_5$, the precedence of the point or points must be determined. A precedence logic circuit shown by the dashed lines in FIG. 6 and identified by the reference numeral 112 determines the precedence of the points in the tag array in the following order: $T_4$ (from the present cell segment) $T_1$, $T_2$ and $T_3$ (from the previous cell segment).

The precedence logic shown within block 112 is employed to handle the specific situation in which more than one of the outputs from the logic circuits S1 through S4 is high. In this situation, it is necessary to determine the first one in precedence.

The output from the precedence logic circuit 112 on output line 114 is ONE (high) if there is no point in $T_4$, $T_1$, $T_2$, or $T_3$ which is of the same type as that of $T_5$ and ZERO (low) if there is a point which is the same as $T_5$. However, if $T_4$ is the first point which is the same type as $T_5$, the precedence logic circuit 112 produces a high "ONE" output on output lead 116 which actuates a corresponding gate 118. With gate 118 actuated, the particular tag or number in $T_4$ is gated onto bus 120 and back into point $T_5$ in the tag array.

If the particular point in $T_4$ was not the same type as that in $T_5$, the precedence logic circuit 112 next examines the type of the point in $T_1$. A corresponding circuit is provided for the $T_1$ point in the tag array with gate 122 being actuated by the output from the precedence logic circuit 112 on output line 124. Thus, if the points $T_1$ and $T_5$ are of the same type, and $T_1$ and $T_4$ are not of the same type, the number of particular tag in $T_1$ is gated through gate 122 onto bus 120 and then into $T_5$. A similar arrangement is also provided for the tag array point $T_2$ through output line 126 and gate 128 and for tag array point $T_3$ through output line 130 and gate 132.

If there is no point in the tag array which is of the same type as $T_5$, the output on lead 114 from the precedence logic circuit will be high and this output is fed to red and white cell and background counter AND gates 134, 136 and 136b, respectively. The second input for each AND gate is the corresponding count red signal count white signal or count background signal obtained from the circuitry shown in FIG. 5. If the count red signal is present, AND gate 134 produces a ONE output on line 138 which is used to increment the red blood cell counter to the next number. The output from AND gate 134 is also used to actuate a gate 140 which gates this next red blood cell number from counter 97 onto bus 120 and thus into tag array point $T_5$. A similar arrangement is provided for the white blood cell counter 95 through AND gate output line 142 and gate 144, and background counter 97b through AND gate output line 142b and gate 144b.

The output from the precedence logic circuit 112 on line 114 is also applied to a NEW number logic circuit shown by the dashed lines in FIG. 6 and identified by the reference numeral 146. The NEW number logic circuit 146 maintains a record of the assignment of a new number to a string of points on the "present" line of analysis. The present line is represented in part within the tag array by points $T_5$ and $T_4$ while the "previous" line appears in part in the tag array points $T_3$, $T_2$ and $T_1$.

The NEW logic circuit 146 is used to distinguish between two cases in which points in the same object have been assigned different numbers. The two cases can be thought of in general terms as the "sloping line" case the "U-shaped" case.

In the first case, a portion of the particular region under analysis slopes gently upwardly in the direction of the scan. The slope is gradual enough so that three or more points are encountered which are not contiguous to any point of the same type in the previously scanned line. Since the present line points (at least three or more) are not contiguous with the points of the same type in the previous line, the precedence logic, tag array, and the appropriate red or white cell or background counters will assign a "new number" to the present line points. However, in actuality the present line points are a part of the same region as the previous line points. Thus, we have a situation in which the previous line points have been assigned one number while the present line points have been assigned another number although in fact all of the points are part of the same region.

In the second or U-shaped case, the first encountered upstanding leg portion of the "U"-shaped region or object is assigned one number and the second encountered upstanding leg of the U-shaped region or object is assigned another number. Upon subsequent scans, the system will recognize that the two upstanding legs which have been assigned individual numbers are in fact all part of the one particular region or object.

In both cases recognition occurs when points of the same cell type but having different numbers appear in points $T_3$ and $T_5$ in tag array 92. Although the sloping line and U-shaped cases appear the same to the tag array 92, it is expedient to distinguish them and treat them differently. In the case of the sloping line object, the Present line tag or number will be changed to the previous line tag or number by means of the circuitry shown in FIG. 7 and the appropriate red or white cell or background counter will be decremented. In the case of the U-shaped object, the two tags or cell numbers will be EQUATED with each other for purposes of subsequent identification and incorporation of the features stored under each tag or number.

These two cases are distinguished by means of the NEW number logic circuit 146 which comprises OR gates 148 and 150, AND gates 152, 154, and 156, and Flip-Flop 158. The inputs to the NEW number logic circuit 146 are: count red (CNTR) on line 160; count white (CNTW) on input line 162 and count background (CNTB) on line 162b; the output from the precedence logic circuit on line 114 which represents an "Assign New-Number" signal; and, finally, a "change" signal (CHG) on line 164. The change signal is derived from a logic circuit 166 shown in FIG. 7 in accordance with the following truth table:

|  | INPUTS |  | OUTPUTS |  |  |  |
|---|---|---|---|---|---|---|
| Same Type | Same No. | $T_5 > T_3$ | NEW | CHG | EQUATE | DCNT |
| 1 | 0 | 0 | 0 | 0 | 1 | 0 |
| 1 | 0 | 1 | 0 | 1 | 1 | 0 |
| 1 | 0 | $\phi$ | 1 | 1 | 0 | 1 |

$\phi$ = don't care

The NEW Flip-Flop 158 is set whenever the Assign-New-Number signal on the precedence output line 114 is ONE or high. The Assign-New-Number signal is applied as one input on AND gate 152. The second input to the AND gate 152 is provided by the output from OR gate 148. This input is ONE (high) whenever a new number is assigned because either the count red signal, count white signal, or count background signal on OR gate input lines 160, 162 and 162b, respectively, is also high. The output from AND gate 152 is applied as one input to OR gate 150. Thus, if the output from AND gate 152 is high the output from OR gate 150 will also be high. The outputs from OR gate 148 and 150 are ANDed by AND gate 154 thereby producing a high output on line 168 which sets the NEW Flip-Flop 158.

The Flip-Flop 158 maintains itself in the set condition as long as either a count red, a count white or count background signal is present on lines 160, 162 and 162b. If an object-to-zero background (or cell-to-zero background) transition occurs, it can be seen that the count red, count white and count background signals will be low on OR gate input lines 160, 162 and 162b thereby allowing the NEW Flip-Flop 158 to reset. The Flip-Flop 158 also can be reset by a change signal (CHG) on line 164.

For certain complex scenes, the NEW number logic circuit 146 preferably should be triplicated with input OR gate 148 omitted and the inputs 160, 162 and 162b going directly into the triplicated AND gates 152 and 154, the outputs from the triplicated NEW FFs being ORed together into logic circuit 166.

Referring now to FIG. 7 there is shown in block form additional circuitry that operates in conjunction with the tag array 92 and line delay 94. For purposes of clarity, this circuitry was omitted from FIG. 6 and is shown in FiG. 7.

For the sloping line case, the circuitry shown in FIG. 7 (including the previously discussed logic circuit 166) performs the following operations: (1) changes the tag or region number in $T_5$ to the tag or region number in $T_3$; (2) decrements the appropriate red or white blood cell or background counter; and, (3) when appropriate, changes the tag or region numbers in $T_4$ and in the line delay 94 to the tag or region number in $T_3$.

In the case of the U-shaped cell or object, the logic circuit 166 produces an EQUATE signal and, when appropriate, changes tag or region numbers in $T_5$, $T_4$, and the line delay 94 to the tag or region number in $T_3$. The EQUATE signal causes the cell tags in $T_3$ and $T_5$ to be pushed on to a equate stack (not shown) in the main memory (FIG. 9). The change signal (CHG) from logic circuit 166 on line 170 gates the $T_3$ tag or region number on bus 172 through gate 176 onto $T_5$. The tag or region number on $T_3$ bus 172 is also gated into $T_4$ through gate 178. Operation of gate 178 is controlled by means of a logic circuit 180. The truth table for logic circuit 180 is as follows:

| INPUTS |  | OUTPUT |
|---|---|---|
| $T_5 = T_4$ | CHG |  |
| 1 | 1 | 1 |
| 0 | 1 | 0 |
| $\phi$ | 0 | 0 |

It can be seen from the truth table that if T5 is equal to $T_4$, the $T_3$ number on bus 172 is gated through gate 178 into $T_4$. A similar logic circuit 182 controls another gate 184 which gates the $T_3$ number on bus 172 into the first element of the line delay 94. Since the line delay 94 comprises a shift register having a predetermined number of storage elements, the logic 182 and gate 184 is duplicated for a predetermined number of adjacent storage elements in the shift register 94. This additional circuitry is represented in FIG. 7 by the continuing three dots. The purpose of the logic associated with the shift register line delay 94 is to correct the improperly numbered present line points in $T_5$, $T_4$, and the line delay 94. Note that these present points actually should have the same number as the previous line point in $T_3$.

The logic circuit 166 also generates a "down count" or counter decrement signal (DCNT) in accordance with the truth table set forth above. The down count signal is applied as one input to two AND gates 186 and 188 shown in FIG. 6. AND gate 186 controls the operation of the red blood cell counter 97. The second input to AND gate 186 is the count red signal (CNTR). In a similar manner AND gate 188 decrements the white blood cell counter 95 AND gate 188b decrements the background counter 97b.

In a simplified version of the preferred embodiment, the NEW Flip-Flop and its associated circuitry, the DCNT signal, and the CHANGE signal operating upon the elements of line delay 94 can be eliminated, any occurance of the same region type but different numbers in $T_3$ and $T_5$ being EQUATED. However, this can result in the features for a particular cell being stored under a number of cell number tags. This in turn eventually increases the work of the computer in sorting out these numeric EQUATES.

There remains one special case which should be provided for the case when one or more cells is touching or overlapping an edge of the field. A cell which overlaps the edge of the field will be incomplete and thus not suitable for analysis. This case is provided for by causing the scan and digitize circuitry to output black points during its horizontal and vertical retrace intervals. These points are the first that are encountered at the beginning of a scan of the field, and being black, they look like an object. These points are given the tag number ZERO. Any cell touching the field edge will appear to be part of the same object, and thus will also be assigned tag number Zero. In addition, background points touching the edge of the field are also assigned a zero number. Thus any background region with a non-zero number is not simply connected through background points to the edge of the field. To simplify data handling, special circuitry (not shown) prevents the storage of any data in main memory when the tag number is ZERO. Thus, all regions touching the field's edge are ignored.

Having described in detail the operaton of the circuitry which assigns a tag to each of the identified segments in response to the control signals and sample region classification signals as shown in FIGS. 6 and 7, I will now discuss the utilization of these identification numbers with respect to the scanned image data. Referring back to FIG. 4 for a moment, the Digitized Serial Data Signals A', B', and C' are applied to corresponding storage shift registers 190a, 190b, and 190c. Each shift register has a corresponding line delay 192a, 192b and 192c. The output from each delay is fed back into the corresponding shift register. The delay provided by the signal transit through the lower portion, as viewed in the drawing of shift registers 190 and the line delays 192 correspond to one line width of the scanned image 14. This delay is employed to synchronize the image data signal with the previously discussed control signals.

The output from each shift register on lines 194a, 194b, and 194c is applied as one input to a background subtract circuit 196a, 196b, and 196c. The second input to the background circuit is the associated background density output from histogrammer 40. The output from each of the background subtract circuits 196 is a six-bit digitized signal representing the scanned image data with the background density subtracted therefrom. These outputs are identified as DATA-A, DATA-B and DATA-C.

Referring now to FIG. 8, the partial cell features are compiled for each of the identified and tagged cell and non-zero background segments. The full data signals DATA-A, DATA-B, and DATA-C are inputted to white and red blood cell density summing circuits. As shown in FIG. 8, a separate accumulator 198a, 198b, and 198c is provided for each data channel to sum the densities of the white blood cell nucleus DATA-A, DATA-B, DATA-C. Corresponding accumulators 200a, 200b, and 200c are provided for the white blood cell cytoplasm data. Red blood cell density summation is provided for data channels A and C by accumulators 202a, and 202c. The DATA-A, DATA-B, and DATA-C information is gated into the appropriate accumulators in accordance with the gating control signal count nucleus (CNTN), count cytoplasm (CNTC) and count red (CNTR). These signals are derived from the control logic circuit 86 shown in FIG. 5.

The control signals are also used to gate either the appropriate tag number from the tag array block $T_5$ into white blood cell tag register 204 or red blood cell tag cell register 206. In addition, these control signals are also used to increment either nucleus, cytoplasm or red blood cell size counters 208, 210, and 212, respectively.

Looking now at the bottom portion of FIG. 8 there are shown three dual perimeter counters 214, 216, and 218 for the white blood cell nucleus perimeter, white blood cell cytoplasm perimeter, and red blood cell perimeter, respectively. Each counter sums the number of straight and diagonal perimeter signals in each cell component type. The dual white blood cell nucleus perimeter counter 214 is incremented by the straight perimeter control signal (STN) and by the diagonal perimeter nucleus control signal (DPB) which are obtained from control logic circuit 76 shown in FIG. 5.

The dual cytoplasm perimeter counter 216 is incremented by the output from two AND gates 218 and 220. AND gate 218 has as its input the straight perimeter, white cytoplasm signal (STWC) which is derived from control logic 82 shown in FIG. 5 and the inverted perimeter inhibit signal (PINH) which is derived from control logic circuit 86 shown in FIG. 5.

Referring back to the truth table for control logic circuit 86, it can be seen that when the perimeter inhibit signal is low or ZERO and the straight perimeter white cytoplasm signal is present, AND gate 218 will produce an output which increments the straight perimeter segment counting portion of the dual cytoplasm perimeter counter 216. AND 220 also utilizes the perimeter inhibit signal together with the diagonal perimeter, white cytoplasm control signal (DPWC) which is derived from the control logic circuit 82 shown in FIG. 5. Similar circuitry is also used for the dual red perimeter counter 218 through AND gates 222 and 224. The corresponding control signals straight perimeter red (SPR) an diagonal perimeter red (DPR) are obtained from control logic circuit 84 shown in FIG. 5.

Referring back for a moment to the tag array shown in FIGS. 6 and 7, if there are no cell points in the tag array blocks $T_4$ and $T_5$ and there are cell points in tag array $T_1$ and $T_2$, the configuration reflects the existence of a perimeter segment from a previous cell on a previous line that was not detected by the system. This situation is handled by the circuitry shown toward the bottom of FIG. 8. The cell tag or number from the $T_2$ block of the tag array 92 is gated into an appropriate nucleus alternate number register 226, a cytoplasm alternate number register 228 or a red blood cell alternate number register 230. The gating signals for the nucleus and cytoplasm alternate number register 226 and 228 comprise the control signals previous row perimeter, nucleus (PRN) and previous row, white cytoplasm (PRWC) which are obtained from control logic circuits 76 and 82, respectively, shown in FIG. 5.

The red blood cell alternate number register number 230 is controlled by the gating signals previous row, red cell (PRR) which is derived from control logic circuit 84 shown in FIG. 5. These control signals are also used to increment corresponding alternate perimeter counters 232, 234, and 236.

At the bottom of FIG. 8 is the circuitry for compiling non-zero background features for red cell control pallor and white cell inclusions. In this embodiment only the area is compiled; other more complex features can of course be included.

Non-zero background size is accumulated in counter 212b which is incremented by control signal CNTB from logic 86 in FIG. 5. In addition, the background tag is gated from $T_5$ in array 92 into register 206b.

Looking now at FIG. 9, the white blood cell portion of the nucleus and cytoplasm counters, accumulators and registers have been duplicated in FIG. 9 with the same reference numerals being used to identify like components. FIG. 9 illustrates the outputs from each of these circuit components. Note that the inputs shown in FIG. 8 have been omitted from FIG. 9. Furthermore, the entire red blood cell and non-zero background portion has been omitted from FIG. 9. However, it should be understood that the same basic circuitry is employed for the handling of the red blood cell data and non-zero background.

FIG. 9 illustrates the use of each region tag to sequentially compile complete cell features from the partial cell features of each identified cell segment having the same cell tag. The outputs from the white blood cell nucleus size counter 208, cytoplasm size counter 210, density accumulators 198$a$ through 198$c$ and 200$a$ through 200$c$, nucleux and cytoplasm perimeter counters 214 and 216, respectively, are shifted into a buffer memory 238 in response to a store white cell signal (STW). The appropriate tag or cell number from the white blood cell register 204 is also shifted into the buffer memory at the same time. The contents of the buffer memory are added into a main memory 240 (which includes a controller) in locations determined by the cell tag. In this way all the partial features having the same cell tag are added to the same locations to produce the complete features for the tagged cell. The main memory controller controls the gating of the buffer memory data into the main memory and adds the buffer contents to the previous contents in the main memory. After a short delay the WBC counters and accumulators are cleared by a "clear" signal produced by delay circuit 242.

It should be noted at this point that the red blood cell and non-zero background information is processed in the same manner through a buffer memory (not shown) into the main memory and controller 240.

The contents of the alternate perimeter counters 232 and 234 for the nucleus and cytoplasm, respectively, are also shifted into another buffer memory 244. In a similar manner, the tag or cell numbers contained in the alternate number registers 226 and 228 are shifted into the buffer memory 244. The alternate perimeter and alternate number data is shifted into the buffer memory 244 in response to the store previous row, nucleus (SPRN) signal or the store previous row, white cytoplasm (SRWC) signal which are obtained from the FIG. 3 logic circuits 76 and 82, respectively. These two signals are applied as one input to an AND gate 246 whose output controls the shifting of the alternate perimeter and alternate number data into the buffer memory 244. The second input to AND gate 246 is provided by the output of an OR gate 248 whose inputs comprise the outputs of the nucleus alternate number register 226 and the cytoplasm alternate number register 228.

The operation of the alternate perimeter circuitry shown in the bottom of FIG. 9 can best be understood by looking back for a moment at FIGS. 5 and 6. Assume that the five block delay arrays 66, 68, and 70 in FIG. 5 and the tag array 92 shown in FIG. 6 contain nuclear points in blocks numbers 4 and 5, e.g. $T_4$ and $T_5$, while the block numbers 1, 2, and 3 contain no nuclear points. In this situation, it is clear that a perimeter segment has been encountered. However, let us assume that all five blocks have nuclear points, but the points in the scanned image just below points 4 and 5 have background points (this will be recognized on the next line scan). The perimeter segment will be recognized only when the points in $T_5$ and $T_4$ are shifted through to the tag array $T_3$ and $T_2$ and $T_1$ and the background points just below points $T_5$ and $T_4$ are placed in $T_5$ and $T_4$. It will be appreciated that at this time it is too late to recognize this special case for the perimeter segment by means of the regular circuitry. The additional alternate perimeter circuitry shown in FIGS. 8 and 9 is employed to determine and compile the extra perimeter segments produced in this specific situation.

Referring back to FIG. 9, the contents of the buffer memory are added into the main memory in response to the main memory controller. After a suitable delay produced by delay circuit 250, the alternate perimeter counters are cleared by the "clear-A" signal.

It remains to describe the operation of a one-bit LINK registers 252, 252$b$ in FIG. 8. The LINK 252 is set by logic 86 in FIG. 5 when it appears that a nucleated red blood cell has been encountered, or when it is not possible to tell whether a nucleated RBC or a WBC which touches an RBC has been encountered. Nucleated RBC's have the property of having both a nucleus and hemoglobin in their cytoplasm. Thus, parts of the cell will be analyzed by the RBC portion of the hardware in FIG. 8, and part by the WBC hardware. When the data is stored for this type cell, both the WBC and RBC portions of the data must be stored. Thus a "1" in the link register 252 causes a "STW" and "STR" signal when either is present thereby effecting the desired dual storage. In addition the link register 252 set causes the two region tags from 204 and 206 to be entered on a link push down stack in computer main memory.

The LINK 252$b$ is set by the LINK signal from logic 86 in FIG. 5 ANDed with the CNTB signal, when a region of non-zero background is adjacent to a cell region. It is not always possible to determine at that time whether the non-zero background is a real red cell central pallor or white cell inclusion, or whether it will subsequently touch zero background and thus become part of the true scene background. To save the information for future reference, the link register 252$b$ set causes the two region tags from $T_4$ and $T_5$ to be entered into the same link push down stack in the computer main memory 240. In this way the cell region is "associated" with the non-zero background region for the purpose of compiling complete feature for the cell and its inclusions.

Features for various part of different objects stored under different tags (red cell, white cell, and non-zero background) are compiled using the information in the Equate and Link stacks, and these cells are then further classified using the compiled features. This classification is performed by the computer CPU (FIG. 1) using instructions in the control memory, while the scanner is moved to a new field on the sample. After the classification is completed, the area in the main memory reserved for complete features is zeroed in readiness for the features from the cells in the next field to be analyzed. This process is repeated until sufficient cells have been examined, at which time a summary of the data is output on a data output device.

It will be appreciated from the foregoing description that the preferred embodiment is one specific example of a more general method and apparatus for subject analysis characterized by compilation of partial features from one or more signals representing the sample.

In the preferred embodiment, partial features are compiled from a raster scanned signal representing the sample using control signals derived from the previously mentioned color algebra. However, an alternative version of the invention can be employed to compile features for the various regions of a sample from a signal representing a sample entrained in a gas or liquid flowing past a fixed sensor, using control signals derived from that signal, or from a color algebra.

In addition, the preferred embodiment incorporates the compilation of complete features from partial features which represent the size, perimeter, and density of the cell at the various wavelength bands. From these measurements can be derived features representing the average color and shape of the various cell regions. However, these features are only a few of the many features representing shape, color and density which can be compiled using my invention. Features representing cell characteristics other than size, shape, perimeter length, density and color also can be compiled with my invention, depending on the desires of the user. It should be understood that the particular set of features described in connection with the preferred embodiment was chosen for purposes of illustration and should not be considered as limiting the scope of the invention.

Having described in detail a preferred embodiment of my invention, it will be apparent to those skilled in the art that numerous modifications can be made therein without departing from the scope of the invention as defined in the following claims.

What I claim and desire to secure by Letters Patent of the United States is:

1. A method of sample analysis comprising the steps
   1. illuminating a particle containing sample with light which is modified by the sample;
   2. producing a first signal representing a first predetermined wavelength band of the sample modified light at a region in said sample;
   3. producing a second signal representing a second predetermined wavelength band of the sample modified light at said region, said first and second wavelength bands being selected to produce a differential contrast between said region and at least one other region in said particle sample; and,
   4. algebraically combining with thresholding said first and second signals to classify said sample region in at least one of a predetermined number of categories.

2. A method of sample analysis comprising the steps of:
   1. illuminating a sample with light which is modified by the sample;
   2. producing first and second raster scanned signals representing corresponding first and second predetermined wavelength bands of the sample modified light, said first and second wavelength bands being selected to produce a differential contrast between at least two different regions in said sample;
   3. algebraically combining with thresholding said first and second signals to produce control signals;
   4. utilizing said control signals to identify sample segments in the raster scanned signals;
   5. utilizing said control signals to compile partial sample features from the raster scanned signals on a line-by-line basis for predetermined but not all of said identified sample segments;
   6. generating sample tags;
   7. assigning a sample tag to at least each of said predetermined identified sample segments; and,
   8. utilizing each sample tag to sequentially compile complete sample features from the partial sample features of said predetermined identified sample segments having the same sample tag.

3. A method of blood cell analysis comprising the steps of:
   1. illuminating a blood cell sample with light which is modified by the sample;
   2. producing first and second raster scanned signals representing corresponding first and second predetermined wavelength bands of the sample modified light, said first and second wavelength bands being selected to produce a differential contrast between at least two different regions in said sample;
   3. algebraically combining with thresholding said first and second signals to produce sample region classification signals;
   4. algebraically combining said sample region classification signals to produce control signals;
   5. utilizing said control signals to identify region segments in the raster scanned signals;
   6. utilizing said control signals to compile partial cell features from the raster scanned signals on a line-by-line basis using at least some identified region segments;
   7. generating region tags;
   8. assigning a region tag to each of said identified region segments; and,
   9. utilizing said region tags to sequentially compile complete cell features from the partial cell features of said at least some identified region segments having the same region tag.

4. A method of blood cell analysis comprising the steps of:
   1. illuminating a blood cell sample with light which is modified by the sample;
   2. producing first and second raster scanned signals representing corresponding first and second predetermined wavelength bands of the sample modified light, said first and second wavelength bands being selected to produce a differential contrast between at least two different regions in said sample;
   3. thresholding said first and second raster scanned signals to produce corresponding first and second thresholded signals;
   4. algebraically combining said first and second thresholded signals to produce sample region classification signals;
   5. algebraically combining said sample region classification signals to produce control signals;
   6. utilizing said control signals to identify region segments in the raster scanned signals;
   7. utilizing said control signals to compile partial cell features from the raster scanned signals on a line-by-line basis, using at least some identified region segments;
   8. generating region tags;
   9. assigning a region tag to each of said identified region segments in response to said control signals and said sample region classification signals; and,
   10. utilizing said region tags to sequentially compile complete cell features from the partial cell features of said at least ome identified region segments having the same region tag.

5. A method of blood cell analysis comprising the steps of:

1. illuminating a blood cell sample with light which is modified by the sample;
2. producing first, second and third raster scanned signals representing corresponding first, second and third predetermined wavelength bands of the sample modified light, said first, second and third wavelength bands being selected to produce a differential contrast between at least two different regions in said sample;
3. thresholding said first, second and third raster scanned signals to produce corresponding first, second and third thresholded signals;
4. algebraically combining said first, second and third threshold signals to produce sample region classification signals;
5. algebraically combining said sample region classification signals to produce control signals;
6. delaying said sample region classification signals to re-establish their vertical connection;
7. utilizing said control signals to identify cell and background segments in the raster scanned signals;
8. utilizing said control signals to compile partial cell features from the raster scanned signals on a line-by-line basis for each said identified cell segment and for at least some identified background segments;
9. generating cell and background region tags;
10. assigning cell and background region tags to each of said identified cell and background segments respectively in response to said control signals and said sample region classification signals;
11. associating at least one of said background region tags with at least one of said cell region tags; and,
12. utilizing each cell region tag to sequentially compile complete cell features from the partial cell features of each identified cell segment having the same cell region tag and from each identified background segment having a background region tag which was associated with said same cell region tag.

6. A method of blood cell analysis comprising the steps of:
1. staining a blood cell sample;
2. illuminating the stained blood cell sample with light which is modified by the sample;
3. raster scanning an area of said stained blood cell sample to produce a first, second and third raster scanned signals representing corresponding first, second and third predetermined wavelength bands of the sample modified light, said first, second and third wavelength bands being selected to produce a differential contrast between at least two different regions in said sample;
4. digitizing said first, second and third raster scanned signals to produce corresponding first, second and third digitized serial data signals;
5. thresholding said first, second and third digitized serial data signals to produce first, second and third thresholded signals;
6. algebraically combining said first, second and third thresholded signals to produce sample region classification signals;
7. algebraically combining said sample region classification signals to produce first control signals;
8. delaying said sample region classification signals to re-establish their vertical connection;
9. algebraically combining the vertically connected sample region classification signals to produce second control signals;
10. utilizing said first control signals to identify cell and background segments in the digitized serial data signals;
11. utilizing said first and second control signals to compile partial cell features from the digitized serial data signals on a line-by-line basis for each said identified cell segment and for at least some identified background segments;
12. generating cell region tags;
13. generating first and second classes of background region tags;
14. assigning a cell tag to each of said identified cell segments in response to said control signals and said sample region classification signals and as a function of the existence of a previously assigned cell tag, said previously assigned cell tag being delayed to re-establish its vertical connection with the identified cell segment;
15. Assigning a first or second class of background region tag to each of said identified background segments in response to said control signals and said sample region classification signals and as a function of the existence of a previously assigned background region tag, said first class of background region tags being assigned to background regions which are simply connected to an edge of the raster scanned area, said second class of background region tags being assigned to background regions which are not simply connected by previously identified and tagged background segments to an edge of the raster scanned area, said previously assigned background region tags being delayed to re-establish their vertical connection with the identified background segment;
16. associating at least one of said second class of background region tags with at least one of said cell region tags;
17. utilizing each cell region tag to sequentially compile complete cell features from the partial cell features of each identified cell segment having the same cell region tag and from each identified background segment having a second class of background region tag which was associated with said same cell region tag.

7. An apparatus for sample analysis comprising:
1. means for illuminating a sample with light which is modified by the sample;
2. means for producing first and second scanned signals representing corresponding first and second predetermined wavelength bands of the sample modified light, said first and second wavelength bands being selected to produce a differential contrast between at least two different regions in said sample;
3. means for algebraically combining with thresholding said first and second scanned signals to produce sample region classification signals;
4. means responsive to said sample region classification signals for identifying sample segments in the scanned signals;
5. means responsive to said sample region classification signals for compiling partial sample features from the scanned signals on a line-by-line basis for predetermined but not all of said identified sample segments and;

6. means for generating sample tags;
7. means for assigning a sample tag to at least each of said predetermined identified sample segments; and,
8. means utilizing each sample tag for sequentially compiling complete sample features from the partial sample features of said predetermined identified sample segments having the same sample tag.

8. An apparatus for blood cell analysis comprising:
1. means for illuminating a blood cell sample with light which is modified by the sample;
2. means for producing first and second raster scanned signals representing corresponding first and second predetermined wavelength bands of the sample modified light, said first and second wavelength bands being selected to produce a differential contrast between at least two different regions in said sample;
3. means for algebraically combining with thresholding said first and second signals to produce sample region classification signals;
4. means for algebraically combing said sample region classification signals to produce control signals;
5. means responsive to said control signals for identifying region segments in the raster scanned signals;
6. means responsive to said control signals for compiling partial cell features from the raster scanned signals on a line-by-line basis using at least some identified region segments;
7. means for generating region tags;
8. means for assigning a region tag to each of said identified region segments in response to said control signals and said sample region classification signals; and,
9. means utilizing said region tags for sequentially compiling complete cell features from the partial cell features of said at least some identified region segments having the same region tag.

9. An apparatus for blood cell analysis comprising;
1. means for illuminating a blood cell sample with light which is modified by the sample;
2. means for producing first, second and third raster scanned signals representing corresponding first, second and third predetermined wavelength bands of the sample modified light, said first, second and third wavelength bands being selected to produce a differential contrast between at least two different regions in said sample;
3. means for thresholding said first, second and third raster scanned signals to produce corresponding first, second and third thresholded signals;
4. means for algebraically combining said first, second and third threshold signals to produce sample region classification signals;
5. means for algebraically combining said sample region classification signals to produce control signals;
6. means for delaying said sample region classification signals to re-establish their vertical connection;
7. means responsive to said control signals for identifying cell and background segments in the raster scanned signals;
8. means responsive to said control signals for compiling partial cell features from the raster scanned signals on a line-by-line basis for each said identified cell segment and for at least some identified background segments;
9. means for generating cell and background region tags;
10. means for assigning cell and background region tags to each of said identified cell and background segments respectively in response to said control signals and said sample region classification signals;
11. means for associating at least one of said background region tags with at least one of said cell region tags; and,
12. means utilizing each cell region tag for sequentially compiling complete cell features from the partial cell features of each identified cell segment having the same cell region tag and from each identified background segment having a background region tag which was associated with said same cell region tag.

10. An apparatus for blood cell analysis comprising:
1. means for illuminating a stained blood cell sample with light which is modified by the sample;
2. means for raster scanning an area of said stained blood cell sample to produce a first, second and third raster scanned signals representing corresponding first, second and third predetermined wavelength bands of the sample modified light, said first, second and third wavelength bands being selected to produce a differential contrast between at least two different regions in said sample;
3. means for digitizing said first, second and third raster scanned signals to produce corresponding first, second and third digitized serial data signals;
4. means for thresholding said first, second and third digitized serial data signals to produce first, second and third thresholded signals;
5. means for algebraically combining said first, second and third thresholded signals to produce sample region classification signals;
6. means for algebraically combining said sample region classification signals to produce first control signals;
7. means for delaying said sample region classification signals to re-establish their vertical connection;
8. means for algebraically combining the vertically connected sample region classification signals to produce second control signals;
9. utilizing said first control signals to identify cell and background segments in the digitized serial data signals;
10. means responsive to said first and second control signals for compiling partial cell features from the digitized serial data signals on a line-by-line basis for each said identified cell segment and for at least some identified background segments;
11. means for generating cell region tags;
12. means for generating first and second classes of background region tags;
13. means for assigning a cell tag to each of said identified cell segments in response to said control signals and said sample region classification signals and as a function of the existence of a previously assigned cell tag, said previously assigned cell tag being delayed to re-establish its vertical connection with the identified cell segment;
14. means for assigning a first or second class of background region tag to each of said identified background segments in response to said control signals and said sample region classification signals and as a function of the existence of a previously assigned background region tag, said first class of background region tags being assigned to background regions which are simply connected to an edge of the raster scanned area, said second class of background region tags being assigned to background regions which are not simply connected by previously identified and tagged background segments to an edge of the raster scanned area, said previously assigned background region tags being delayed to re-establish their vertical connection with the identified background segment;

15. means for associating at least one of said second class of background region tags with at least one of said cell region tags;

16. means for utilizing each cell region tag for sequentially compiling complete cell features from the partial cell features of each identified cell segment having the same cell region tag and from each identified background segment having a second class of background region tag which was associated with said same cell region tag.

11. The method of claim 2 wherein partial features are compiled for non-zero background identified sample segments, but not for zero background identified sample segments.

12. The apparatus of claim 7 wherein said partial sample feature compiling means compiles partial sample features for non-zero background identified sample segments, but not for zero background identified sample segments.

* * * * *